United States Patent
Moreau-Gaudry et al.

(10) Patent No.: US 10,028,722 B2
(45) Date of Patent: Jul. 24, 2018

(54) METHODS AND APPARATUS FOR ASSISTING CARTILAGE DIAGNOSTIC AND THERAPEUTIC PROCEDURES

(75) Inventors: Alexandre Marie Moreau-Gaudry, Meylan (FR); Philippe Cinquin, St. Nazaire les Eymes (FR); Christopher Plaskos, New York, NY (US); Carinne Granchi, Weston, FL (US); Ronald S. Adler, Larchmont, NY (US)

(73) Assignees: Hospital for Special Surgery, New York, NY (US); Perception Raisonnement Action En Medecine, Raynham, MA (US); L'Universite Joseph Fourier (FR)

(*) Notice: Subject to any disclaimer, the term of this patent is extended or adjusted under 35 U.S.C. 154(b) by 801 days.

(21) Appl. No.: 12/679,808

(22) PCT Filed: Sep. 24, 2008

(86) PCT No.: PCT/US2008/077454
§ 371 (c)(1),
(2), (4) Date: Jun. 24, 2010

(87) PCT Pub. No.: WO2009/042644
PCT Pub. Date: Apr. 2, 2009

(65) Prior Publication Data
US 2010/0256504 A1    Oct. 7, 2010

Related U.S. Application Data

(60) Provisional application No. 60/974,963, filed on Sep. 25, 2007.

(51) Int. Cl.
*A61B 6/00* (2006.01)
*G06G 7/48* (2006.01)
(Continued)

(52) U.S. Cl.
CPC .............. *A61B 8/08* (2013.01); *A61B 5/0066* (2013.01); *A61B 5/064* (2013.01); *A61B 5/1127* (2013.01);
(Continued)

(58) Field of Classification Search
CPC combination set(s) only.
See application file for complete search history.

(56) References Cited

U.S. PATENT DOCUMENTS 4,650,302 A    3/1987  Grant
5,447,154 A *  9/1995  Cinquin et al. ............... 600/429
(Continued)

FOREIGN PATENT DOCUMENTS

FR         1222636        7/2002
WO      2006087437        8/2006

OTHER PUBLICATIONS

Farr et al., "Patient Evaluation and Surgical Decision Making", the Journal of Knee Surgery, Oct. 2004, vol. 17, No. 4.*
(Continued)

*Primary Examiner* — Serkan Akar
*Assistant Examiner* — Farshad Negarestan
(74) *Attorney, Agent, or Firm* — Kim Winston LLP

(57) ABSTRACT

In one embodiment of the present invention, a method is provided for assisting cartilage diagnostic and therapeutic procedures and includes the steps of acquiring 3D osteocartilaginous parameters by using multimodal 3D tracked devices; incorporating these parameters into a volumic anatomic osteocartilaginous model from which a bone tracking virtual real-time environment is built; three-dimensionally computing an osteocartilaginous quality score from this multiparametric 3D osteocartilaginous model; providing real-time navigation in this 3D virtual environment in order to make ongoing therapeutic assessments and adjustments;
(Continued)

and updating steps 1 to 3 according to the performed therapy. It will be appreciated that the above steps are compatible with arthroscopic procedures involving cartilage.

27 Claims, 10 Drawing Sheets

(51) Int. Cl.
| | |
|---|---|
| A61B 8/08 | (2006.01) |
| A61B 5/00 | (2006.01) |
| A61B 5/06 | (2006.01) |
| A61B 5/11 | (2006.01) |
| A61B 8/12 | (2006.01) |
| A61B 8/00 | (2006.01) |
| G09B 23/28 | (2006.01) |
| A61B 34/20 | (2016.01) |
| A61B 5/107 | (2006.01) |
| A61B 34/10 | (2016.01) |
| A61B 90/00 | (2016.01) |

(52) U.S. Cl.
CPC .......... A61B 5/4514 (2013.01); A61B 5/6852 (2013.01); A61B 6/5247 (2013.01); A61B 8/12 (2013.01); A61B 8/4245 (2013.01); A61B 8/462 (2013.01); A61B 8/5238 (2013.01); A61B 34/20 (2016.02); G09B 23/28 (2013.01); A61B 5/1075 (2013.01); A61B 5/4504 (2013.01); A61B 5/4528 (2013.01); A61B 6/502 (2013.01); A61B 2034/105 (2016.02); A61B 2090/378 (2016.02)

(56) References Cited

U.S. PATENT DOCUMENTS

| | | | | |
|---|---|---|---|---|
| 5,564,437 | A * | 10/1996 | Bainville et al. | 600/587 |
| 6,016,439 | A * | 1/2000 | Acker | 600/411 |
| 6,161,080 | A * | 12/2000 | Aouni-Ateshian et al. | 703/11 |
| 6,205,411 | B1 | 3/2001 | DiGioia et al. | 703/11 |
| 6,246,483 | B1 * | 6/2001 | Smith et al. | 356/520 |
| 6,419,654 | B1 * | 7/2002 | Kadan | 604/27 |
| 6,697,664 | B2 * | 2/2004 | Kienzle, III et al. | 600/427 |
| 6,934,018 | B2 | 8/2005 | Shaw et al. | |
| 7,167,742 | B2 * | 1/2007 | Camacho et al. | 600/473 |
| 7,184,814 | B2 * | 2/2007 | Lang et al. | 600/416 |
| 7,227,981 | B1 * | 6/2007 | Fleute et al. | 382/132 |
| 7,239,908 | B1 * | 7/2007 | Alexander et al. | 600/427 |
| 7,881,768 | B2 * | 2/2011 | Lang et al. | 600/407 |
| 7,949,386 | B2 * | 5/2011 | Buly et al. | 600/427 |
| RE43,282 | E | 3/2012 | Alexander et al. | 600/427 |
| 8,170,649 | B2 * | 5/2012 | Johansson et al. | 600/476 |
| 8,265,730 | B2 * | 9/2012 | Alexander et al. | 600/410 |
| 8,771,978 | B2 * | 7/2014 | Ragan | 435/40.52 |
| 8,801,720 | B2 * | 8/2014 | Park et al. | 606/88 |
| 2002/0087274 | A1 | 7/2002 | Alexander et al. | 702/19 |
| 2002/0164651 | A1 * | 11/2002 | Steinbeck | 435/7.1 |
| 2002/0177770 | A1 * | 11/2002 | Lang | A61B 5/055 600/410 |
| 2003/0035773 | A1 | 2/2003 | Sofia Totterman et al. | 424/9.1 |
| 2003/0036083 | A1 * | 2/2003 | Tamez-Pena et al. | 435/6 |
| 2003/0055502 | A1 * | 3/2003 | Lang et al. | 623/16.11 |
| 2003/0176783 | A1 * | 9/2003 | Hu | 600/429 |
| 2003/0216669 | A1 * | 11/2003 | Lang et al. | 600/587 |
| 2004/0030245 | A1 * | 2/2004 | Noble et al. | 600/426 |
| 2004/0066955 | A1 * | 4/2004 | Tamez-Pena et al. | 382/128 |
| 2004/0147830 | A1 * | 7/2004 | Parker et al. | 600/407 |
| 2004/0153079 | A1 * | 8/2004 | Tsougarakis et al. | 606/77 |
| 2004/0167390 | A1 * | 8/2004 | Alexander et al. | 600/410 |
| 2004/0193048 | A1 * | 9/2004 | Tsoref | 600/437 |
| 2004/0236424 | A1 * | 11/2004 | Berez et al. | 623/14.12 |
| 2004/0242987 | A1 * | 12/2004 | Liew et al. | 600/407 |
| 2005/0075632 | A1 * | 4/2005 | Russell et al. | 606/53 |
| 2005/0101966 | A1 * | 5/2005 | Lavallee | 606/102 |
| 2005/0119587 | A1 * | 6/2005 | Roessler et al. | 600/562 |
| 2005/0228270 | A1 * | 10/2005 | Lloyd et al. | 600/424 |
| 2005/0245821 | A1 | 11/2005 | Govari et al. | |
| 2005/0267584 | A1 * | 12/2005 | Burdulis et al. | 623/20.19 |
| 2006/0142657 | A1 * | 6/2006 | Quaid et al. | 600/424 |
| 2006/0161051 | A1 * | 7/2006 | Terrill-Grisoni et al. | 600/300 |
| 2006/0161052 | A1 * | 7/2006 | Colombet et al. | 600/300 |
| 2006/0247864 | A1 * | 11/2006 | Tamez-Pena et al. | 702/19 |
| 2006/0250300 | A1 | 11/2006 | Laroche | |
| 2006/0257379 | A1 * | 11/2006 | Giordano et al. | 424/93.7 |
| 2007/0015995 | A1 * | 1/2007 | Lang et al. | 600/407 |
| 2007/0078334 | A1 * | 4/2007 | Scully et al. | 600/424 |
| 2007/0106128 | A1 * | 5/2007 | Lavallee | 600/300 |
| 2007/0121121 | A1 * | 5/2007 | Wilhelm et al. | 356/511 |
| 2007/0167681 | A1 | 7/2007 | Gill et al. | |
| 2007/0179381 | A1 * | 8/2007 | Johansson et al. | 600/476 |
| 2007/0239153 | A1 * | 10/2007 | Hodorek et al. | 606/41 |
| 2007/0249967 | A1 | 10/2007 | Buly et al. | |
| 2007/0276224 | A1 * | 11/2007 | Lang et al. | 600/410 |
| 2008/0004633 | A1 * | 1/2008 | Arata et al. | 606/130 |
| 2009/0018445 | A1 * | 1/2009 | Schers et al. | 600/437 |
| 2009/0076371 | A1 * | 3/2009 | Lang et al. | 600/407 |
| 2009/0190815 | A1 * | 7/2009 | Dam et al. | 382/131 |
| 2010/0234770 | A1 | 9/2010 | Colombet et al. | |
| 2010/0256504 | A1 | 10/2010 | Moreau-Gaudry et al. | |
| 2010/0286519 | A1 * | 11/2010 | Lee et al. | 600/439 |
| 2011/0196377 | A1 * | 8/2011 | Hodorek et al. | 606/87 |
| 2011/0208256 | A1 * | 8/2011 | Zuhars | 606/86 R |
| 2011/0257518 | A1 | 10/2011 | Buly et al. | |
| 2012/0294498 | A1 * | 11/2012 | Popovic | 382/128 |

OTHER PUBLICATIONS

International Search Report for International Application No. PCT/US08/77454 dated Aug. 27, 2009.
Written Opinion for International Application No. PCT/US08/77454 dated Aug. 27, 2009.
Office Action dated Aug. 12, 2009 in U.S. Appl. No. 11/299,287.
Fleute, Markus et al., "Incorporating a statistically based shape model into a system for computer-assisted anterior curciate ligament surgery" Medical Image Analysis vol. 3, No. 3 pp. 209-222, (1999).
Scuderi, Giles R. et al., "Classification of Knee Ligament Injuries", Surgery of the knee, pp. 585-599.
Marcos Agus, Andrewa Giachetti, Enrico Gobbetti, Gianluigi Zanetti, Antonio Zorcolo, Bruno Picasso, Stefano Sellari Franceschini, "A haptic model of a bone-cutting burr", 2003, Stud Health Techno Inform, 94:4-10.
Rajeev Kelkar, "Normal and abnormal mechanics of the shoulder: Studies of articular geometry, contact and kinematics", 1996, Columbia University Ph.D. Dissertation, abstract summary.
Extended European Search Report dated Feb. 29, 2012 in European Application No. 08832927.
Yelin, Ph. D., Edward, "Impact of Musculoskeletal Conditions on the Elderly, Geriatric Medicine Today," Mar. 1939, pp. 103-104, 112-113, 117-118, vol. 8, No. 3.
Chen, Thomas Kuiran, et al., "A system for ultrasound-guided computer-assisted orthopaedic surgery," Computer Aided Surgery, 2005, pp. 281-292, vol. 10:5-6, Taylor & Francis.
AxiEM(TM) "Electromagnetic Technology for Stealth Station Navigation System," Medtronic, 2009, pp. 1-12, Medtronic Navigation Inc., USA.
Mercier, Laurence, et al., "A Review of Calibration Techniques for Freehand 3-D Ultrasound Systems," World Federation for Ultrasound in Medicine & Biology, Nov. 2004, pp. 449-471, vol. 31, No. 4, Elsevier, USA.
Rohling, Robert, et al., "A comparison of freehand three-dimensional ultrasound reconstruction techniques," Medical Image Analysis, 1999, pp. 339-359, vol. 3, No. 4, Oxford University Press.
Marston, P.L., Book Reviews, Physical Principles of Medical Ultrasonics, 2nd edition, Nov. 2004, pp. 2707-2708, 116 (5), Acoustical Society of America.

(56) References Cited

OTHER PUBLICATIONS

Saarakkala, Simo, et al., "Quantitative ultrasound imaging detects degenerative changes in articular cartilage surface and subchondral bone," Physics in Medicine and Biology, 2006, pp. 5333-5346, vol. 51, Institute of Physics Publishing Ltd., United Kingdom.
Chiang, Edward H., et al., "Quantitative Assessment of Surface Roughness Using Backscattered Ultrasound: The Effects of Finite Surface Curvature," World Federation for Ultrasound in Medicine & Biology, Sep. 1993, pp. 123-135, vol. 20, No. 2, Elsevier.
Hattori, MD, Koji, et al., "Quantitative Ultrasound Can Assess Living Human Cartilage," The Journal of Bone and Joint Surgery, Incorporated, 2006, pp. 201-212, vol. 88-A, Supplement 4.
Cherin, Emmanuel, et al,, "Evaluation of Acoustical Parameter Sensitivity to Age-Related and Osteoarthritic Changes in Articular Cartilage Using 50-MHZ Ultrasound," World Federation for Ultrasound in Medicine & Biology, Nov. 27, 1997, pp. 341-354, vol. 24, No. 3, Elsevier.
Zheng, Yong-Ping, et al., "Ultrasound elastornicroscopy using water jet and osmosis loading: Potentials for assessment for articular cartilage," Ultrasonics 44, Jun. 28, 2006, pp. e203-e209, Elsevier.
Saarakkala, Simo, et al., "Mechano-acoustic determination of Young's modulus of articular cartilage," Biorheology, 2004, pp. 167-179, vol. 41, IOS Press.
Pan, Yingtian, et al., "Hand-held arthroscopic optical coherence tomography for in vivo high-resolution imaging of articular cartilage," Journal of Biomedical Optics, Oct. 2003, pp. 648-654, vol. 8, No. 4.
Pierce, Mark C., et al., "Endoscopic Polarization-Sensitive Optical Coherence Tomography," Proc. of SPIE, 2006, vol. 6079 607928-1, Coherence Domain Optical Methods and Optial Coherence Tomography in Biomedicine X.
West, P.A., et al., "Fourier Transform Infrared Spectral Analysis of Degenerative Cartilage: An Infrared Fiber Optic Probe and Imaging Study," Applied Spectroscopy, 2004, pp. 376-381, vol. 58, No. 4.
Hung, Y.Y., et al., "Shearography: An Optical Measurement Technique and Applications, Materials Science and Engineering," 2005, pp. 61-87, vol. 49, Elsevier.
Faugeras, Olivier, "Three-Dimensional Computer Vision a Geometric Viewpoint," pp. 8-17 and 33-41, The MIT Press, Cambridge, Massachusetts; London, England.

Goldring, Mary B., "Anticytokine therapy for osteoarthritis," Expert Opinion on Biological Therapy, 2001, pp. 817-829, vol. 1:5, Taylor & Francis Group.
"Bulletin de L'Academie Nationale de Medecine," 2006, vol. 190, No. 7, l'Imprimerie F. Paillart, Paris, France.
Nash Krahn, Katy, et al, "Fluorescently labeled collagen binding proteins allow specific visualization of collagen in tissues and live cell culture," Analytical Biochemistry, 2006, pp. 177-185, vol. 350, Elsevier.
Leroy, Antoine, et al., "Intensity-Based Registration of Freehand 3D Ultrasound and CT-scan Images of the Kidney".
Penney, G. P., et al. "Registration of freehand 3D ultrasound and magnetic resonance liver images," Medical Image Analysis, 2004, pp. 81-91, vol. 8, Elsevier.
Chi, Ying, et al, "Automatic Segmentation of Carthage in MR Images using CDCG: Chessboard Directional Compensated GVF Snakes," IEEE Computer Society, 2006.
Lavallee, Stephane, et al., "Anatomy-Based Registration of Three-Dimensional Medial Images, Range Images, X-Ray Projections, and Three-Dimensional Models Using Octree-Splines," 119, pp. 115-143, MIT Press.
Lavallee, Stephane, et al., "Elastic Registration and Inference Using Oct-Tree Splines,"1999, pp. 283-296 , Academic Press.
Fleute, Markus, et al., "Building a Complete Surface Model from Sparse Data Using Statistical Shape Models: Application to Computer Assisted Knee Surgery, MICCAI '98 Proceedings of the First International Conference on Medical Image Computing and Computer-Assisted Intervention," Oct. 1998, pp. 879-887, Springer-Verlag, London, United Kingdom.
Fleute, Markus, et al., "Incorporating a statistically based shape model into a system for computer-assisted anterior cruciate ligament surgery," Medical Image Analysis, Feb. 1999, pp. 209-222, vol. 3, No. 3, Oxford University Press, United Kingdom.
Fleute, Markus, "Shape Reconstruction for Computer Assisted Surgery based on Non-Rigid Registration of Statistical Models with Intra-Operative Point Data and X-ray Images," Oct. 2001, France.
Brittberg, MD, PhD., Mats, et al., "Evaluation of Cartilage Injuries and Repair, The Journal of Bone and Joint Surgery Incorporated," 2003, pp. 58-69, vol. 85-A, Supplement 2.

* cited by examiner

METHODS AND APPARATUS FOR ASSISTING CARTILAGE DIAGNOSTIC AND THERAPEUTIC PROCEDURES

CROSS-REFERENCE TO RELATED APPLICATION

The present application claims the benefit of U.S. patent application Ser. No. 60/974,963, filed Sep. 25, 2007, which is hereby incorporated by reference in its entirety.

TECHNICAL FIELD

The present invention relates to the field of diagnosis and treatment of articular cartilage diseases, and of navigated arthroscopic procedures. More specifically, it relates to methods and devices for acquiring, incorporating into a 3D osteocartilaginous model, navigating and updating parameters indicative of the quality of the cartilage under examination during arthroscopic procedures.

BACKGROUND

Cartilaginous (hyaline and fibrocartilage) tissue plays a key role in the articular mechanics of a joint and serves two main functions: first, in association with the synovial liquid, it serves as a dynamic function that decreases the friction force applied to the bones constituting the joint; second, it serves as a static function, which enables the transmission, the dispersion and the damping of the applied constraints. Hyaline cartilage is found lining the bearing surfaces of joints. Hyaline cartilage is avascular, and therefore not prone to regeneration. On the contrary, fibrocartilage (e.g. meniscus) is partially vascular and is able to partially or total self repair. In each case, cartilaginous tissue may be affected with lesions, i.e., abnormalities that affect thickness, surface architecture and internal architectures and biochemical constituents. These lesions may lead to altered joint mechanics with significant functional impairment and disability.

Different diseases are encountered in clinical practice that can affect articular cartilage. For instance, osteoarthritis (OA) is the most common disease. It has been estimated that 63 to 85 percent of Americans over age 65 have radiographic signs of OA (See Yelin E. Impact of musculoskeletal conditions on the elderly. Geriatr Med Today. 1989. (8)3:103-18). Cartilage abnormalities may also occur from post-traumatic or inflammatory etiologies, either of which can predispose the individual to develop secondary OA. Assessment of cartilaginous tissue during the different steps of cartilage disease (diagnosis, treatment, follow-up) is currently based on several imaging modalities. For instance, arthroscopy, which enables direct visualization of cartilage and its injuries (e.g. cartilage defects), magnetic resonance imaging (MRI) with different techniques to assess cartilage tissue, ultrasound imaging (US), optical coherence tomography (OCT) and its derivative (for example PS-OCT), and infra-red (IR) spectrometry analysis all may be identified among the different modalities of cartilaginous tissue assessment. Each has its own advantages and limitations.

Several different types of procedures currently exist for the surgical treatment of osteochondral injuries consisting of full-thickness or partial-thickness chondral defects. These include marrow stimulation, autologous chondrocyte implantation, or osteochondral transplantation. Cartilage procedures are most commonly performed in the knee, but can also be performed in the shoulder, hip, ankle and other joints. While much of the focus in cartilage restorative treatment has been on the repair of full-thickness chondral defects, it is now thought that that earlier treatment of cartilage injuries may delay or prevent irreversible damage. The arthroscopic stabilization of partial-thickness chondral defects obviates the need for more invasive procedures such as partial or total joint arthroplasty.

Traditionally, surgeons have used direct visualization to inspect articular cartilage vis a vis arthroscopy. The advent of advanced imaging techniques provides additional information, but ultimately any intervention has relied on direct visualization. This fundamentally requires changes in cartilage surface morphology on a scale large enough to detect visually. Secondly, the geographic nature of articular abnormalities are often more complex than simple geometric shapes, limiting the efficiency of a simple visual assessment. As surgeons begin to treat these complex articular cartilage lesions earlier in the disease process, identifying and precisely mapping the location and extent of such lesions using minimally invasive techniques becomes increasing difficult. Furthermore, locating and evaluating healthy candidate cartilage sites in autologous implantations or transplantations can be a difficult and subjective task with specimens typically obtained from common anatomical areas (i.e., trochlea of the knee), not specific to the individual patient.

Given the extent of the information and lack of visual cues available to the surgeon, it becomes an overwhelming task to integrate the complex 2-D or 3-D geometry and the extent of cartilage disease and produce a rationale for treatment. Presurgical planning becomes necessary, using all the imaging tools available. However, it is necessary to have a method that integrates all this information for them at the time of surgery without the need to mentally create and store a 3D representation of the cartilage surface. Nevertheless, this 3D integration and representation remains challenging and potentially problematic, with possibility of inaccuracy that might negatively impact surgical outcome.

U.S. Pat. No. 7,184,814 B2 entitled "assessing the condition of a joint and assessing cartilage loss" by Philipp Lang et al. discloses methods for assessing cartilage or disease in a living subject. These assessments are based on a three-dimensional volumetric data-set and representation of joint cartilage, including volume, thickness, biochemical contents, or MRI relaxation time of both normal and damaged or diseased cartilage. Correlation of these biomechanical parameters can be obtained with respect to gait analysis by measuring in vivo limb segment movement from skin placed marker clusters (Point Cluster Techniques). Merged or fused with previous morphological and biochemical data, these biomechanical data can therefore be displayed simultaneously, in order to assess the relationships between the cartilage wear and the joint movement.

The authors also describe methods to perform quantitative cartilage follow-up examinations so that cartilage therapies can be monitored. Although different techniques to obtain an image of the cartilage of the joint are mentioned (ultrasound imaging, computed tomography), the authors predominantly rely on 2D or 3D MRI as the method of choice to obtain representations of the cartilage. Although this technique has certain advantages, it also presents significant limitations: it is expensive (in comparison with ultrasound imaging, for instance) and is subject to motion degradation. The ability to perform real-time MR imaging in conjunction with interventional procedures, such as arthroscopy, is not generally available, and could be prohibitively expensive. Thus, it is not generally possible for a surgeon to perform multiple evaluations of cartilage parameters and update a pre-existing model of the joint during arthroscopy. However, a readily updatable cartilage model would offer many advantages to the surgeon who may want to perform multiple cartilage assessments during an arthroscopic repair. A practical example would be optimal placement of a cartilage graft that is implanted into a defect. Real time evaluation of the morphology of the reconstructed surface would be very useful to minimize any residual contour irregularity.

United States Patent Application Publication No. 2005/0257379 entitled 'Surgical system for the preparation of an implant and method for the preparation of an implant' by Giordano et al. discloses a method to quantitatively measure the size, shape, height and/or volume of a cartilage defect. Measurement of the size, shape, height and/or volume of a defect helps the surgeon to select and to prepare an implant so that it better matches and fills the space of the defect. The geometrical parameters of the defect are measured using a position measurement system and a tracked probe having a calibrated tip that is inserted into the joint and positioned in contact with the cartilage surface. The defect can therefore be palpated with the probe tip under arthroscopy, and the boundary line of the defect as outlined by the surgeon can be recorded. Giordano et al. also propose to use an imaging unit connected to the position measuring system to acquire at least one defect image from which boundary information will be extracted. This avoids having to directly contact the cartilage surface. A disadvantage of Giordano's system and method is that the invention provides a tool that the surgeon can use only to outline and size a defect; it provides no assistance to the surgeon to assess the quality of the surrounding cartilage in order to help them determine if it is truly defective or not. It is therefore applicable only to defects in bone/cartilage which are being prepared to be filled by an implant, and it cannot provide any information to aid the assessment of the remaining articular cartilage. In particular, the Giordano system provides no means for quantification of any of the following parameters:

- overall or local cartilage surface texture or roughness;
- distance between the cartilage surface and the underlying subchondral bone, (i.e. the thickness of the remaining cartilage surface);
- bio-material properties of the cartilage such as the cartilage stiffness; and
- cartilage subsurface ultra-structural and biochemical properties.

Finally, no features are provided to help the surgeon visualize and interpret these data on a realistic and precise model of the joint under examination.

It would be of value to have improved methods and/or devices that enable the acquisition, interpretation, and utilization of 3D multimodality data on articular cartilage in an integrated, flexible and updatable manner. This capability assists the arthroscopist in the ongoing assessment of any intervention, as well as the providing an updated model to evaluate the need for any further adjustments to the intervention. All of the abovementioned references are hereby incorporated by reference in their entirety.

SUMMARY

In one embodiment of the present invention, a method is provided for assisting cartilage diagnostic and therapeutic procedures and includes the steps of acquiring 3D osteo-cartilaginous parameters by using multimodal 3D tracked devices; incorporating these parameters into a volumic anatomic osteo-cartilaginous model from which a bone tracking virtual real-time environment is built; three-dimensionally computing an osteo-cartilaginous quality score from this multiparametric 3D osteo-cartilaginous model; providing real-time navigation in this 3D virtual environment in order to make ongoing therapeutic assessments and adjustments; and updating steps 1 to 3 according to the performed therapy. It will be appreciated that the above steps are compatible with arthroscopic procedures involving cartilage.

In addition, a system according to one embodiment of the present invention is robust and not susceptible to motion artifacts that are caused by motion of the patient with respect to an imaging system, by measuring the position of (or tracking) the patient motion with respect to the position of the imaging system and using this relative information to combine image data from subsequent acquisitions.

The system of the present invention allows updating of a osteo-cartilaginous model during a procedure to quantify changes inflicted by the surgeon.

BRIEF DESCRIPTION OF THE DRAWING FIGURES

DETAILED DESCRIPTION OF PREFERRED EMBODIMENTS

The present invention is made up of a number of methods and working components that interact with one another to perform a number of different operations. The headings below merely highlight the various components of the present system, as well as the various operations or tasks performed by the system. As such, these headings do not limit the scope of the present invention.

The system is intended to assist medical diagnostic and therapeutic arthroscopic procedures related to hyaline and/or fibro cartilage. Such a system would be applicable to a variety of medical subspecialties (e.g., orthopedics, radiology, rheumatology, etc.) in which invasive diagnostic and/or therapeutic procedures are performed. Therapeutic procedures can include intra-articular localization for injections, biopsies and other surgical procedures (open, minimally invasive or arthroscopic) that may require direct exposure to the articular surfaces. Surgical procedures can include lavage, debridement, marrow stimulation, autologous chondrocyte implantation, or osteochondral transplantation, and other cartilage restoration procedures.

Overall System

Figure 1:
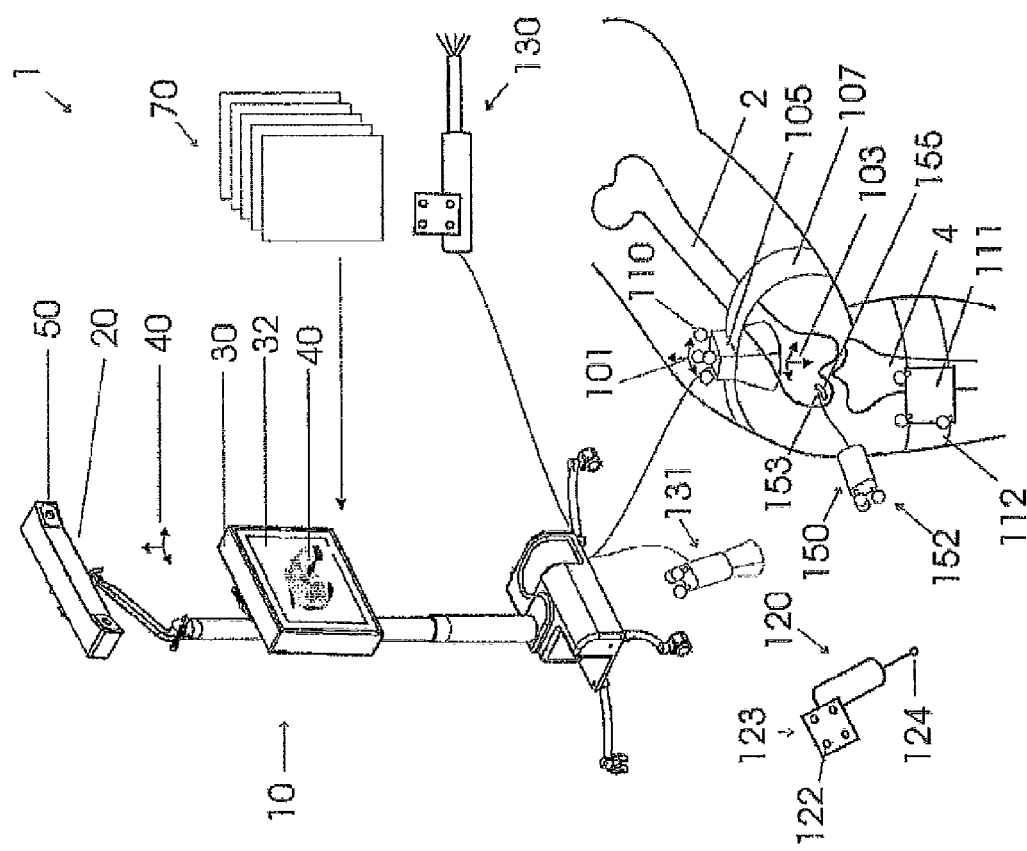
FIG. 1 is a perspective schematic representation of a computer-assisted system for cartilage examination and cartilage procedures according to the present invention.

Referring now to FIG. 1, a system 10 for computer-assisted orthopaedic surgery (CAOS) and diagnostic procedures or examinations is schematically shown. The CAOS system 10 is configured for performing joint preserving and cartilage restoration procedures, including marrow stimulation, autologous chondrocyte implantation, or osteochondral transplantation. The system is also configured for assisting examinations of a patient's joint and the joint cartilage. The system includes a suitable position measuring device that can accurately measure the position of marking elements in three dimensional space (in a common or world reference frame 38 (e.g., three dimensional coordinate system).

Detecting and determining the position and orientation of an object is referred to herein as "tracking" the object. The position measuring device can employ any type of position measuring method as may be known in the art, for example, emitter/detector or reflector systems including optic, acoustic or other wave forms, shape based recognition tracking algorithms, or video-based, mechanical, electromagnetic and radio frequency systems. Examples of such position measuring systems can be found in the following United States Patent Application Publication Nos.: 20050245821 entitled "Position Sensing System for Orthopedic Applications", US 20070078334 DC magnetic-based position and orientation monitoring system for tracking medical instruments, and US 20060250300 entitled "RF system for tracking objects", which are all hereby incorporated by reference in their entirety. For the purposes of illustration, the position measuring system is schematically shown in FIG. 1 as an optical tracking system 20 that includes at least one camera 50 that is in communication with a computer system 30 and positioned to detect light reflected from a number of special light reflecting markers or spheres shown at 110, which have a coordinate system 101 associated with them. In the preferred embodiment of the present invention, however, a less-, minimally-, or non-invasive tracking system is used, such as an electromagnetic tracking system in which the trackers are miniaturized and are not required to be in the line-of-sight of the localizer, nor are they required to be fixed to the bone with large or long pins. The invention can also employ completely non-invasive bone tracking systems, such as ultrasonic tracking systems (for examples, see 'A system for ultrasound-guided computer-assisted orthopedic surgery' by Chen T K Abolmaesumi P, Pichora D R, Ellis R E, Published in: Computer Aided Surgery, Volume 10, Issue 5 & 6 Sep. 2005, pages 281-292, or that described in the U.S. Provisional Patent Application having Ser. No. 60/945,249, entitled Ultrasonic Bone Motion Tracking System by Plaskos et al). Alternatively, in order to avoid invasively fixing the reference body to the bone to track its' position, the reference body can be coupled to the bone using coupling materials or devices, such as, tensioning straps 107, 112, splints, casts, plates 111, etc., that are attached or adhered to the patients skin. The design and shape of the coupling device can be optimized to minimize the motion between the markers and the underlying bone. Markers can also be attached or adhered directly to the skin. The bone could also be immobilized, for example with a leg holder, or to a table. All tools, imaging probes, etc., can then be tracked relative to a reference body attached to the immobilizer or table, or relative to the fixed reference frame of the position measurement system if no bone reference body is used. In any case, a coordinate system 103 can be established that is linked to the bone under study during the procedure (or example, a femur bone 2). All tools, imaging probes, etc., can also be wireless.

To provide precision tracking of objects, markers (e.g. 122, 110) can be rigidly connected together to form trackers or reference bodies, (e.g., 123, 152), and these reference bodies can be coupled to bones, tools, ultrasound probes, arthroscopes, needles, and other objects to be tracked. One such optical device that has been found to be suitable for performing the tracking function is the Polaris™ system from Northern Digital Inc., Ontario, Canada. Tracking and navigation systems are known and described (see, for example, U.S. Patent Application Publication Nos. 2005/0245821 and 2006/0161052, which are also hereby incorporated by reference in their entirety).

Navigating a tracked tool in a 3D environment is referred to herein as visualizing, in real time, a representation of this tool in a representation of this 3D environment. This representation is incorporated into a man-machine interface and presented on a computer display 32, on 3D stereoscopic virtual head-mounted displays, on image overlay or projection systems, digital operating room screens, or the like. The tracked objects and their relative positions can be displayed on a screen 32 that is connected to or integrated into the computer system 30 (for example, a panel PC). In a preferred embodiment, the display is a touch screen which can also be used for data entry.

It will be appreciated that the computer system of the present invention includes a processor and memory (source code is stored in memory and is available to the processor). Software executes in the processor and can include different modules that perform the operations discussed here including the steps that are part of the method of diagnosing and treating articular cartilage diseases by means of a surgical procedure.

The CAOS system 10 is preferably a portable system that is easily transportable to different rooms in a hospital or clinic. Such a system can be placed bedside for use on a patient, and can be wheeled from bed to bed. The system can also be transported from a minor procedures suite to an operating room suite in a hospital. For more information on the portable system, see US Patent Application Publication No. US20070106128, entitled 'Computer Assisted Surgery System' by Lavallee. Other system configurations are possible however, such as that of the StealthStation® AXIEM™ Electromagnetic Navigation Station, marketed by Medtronic, Inc.

Figure 2:
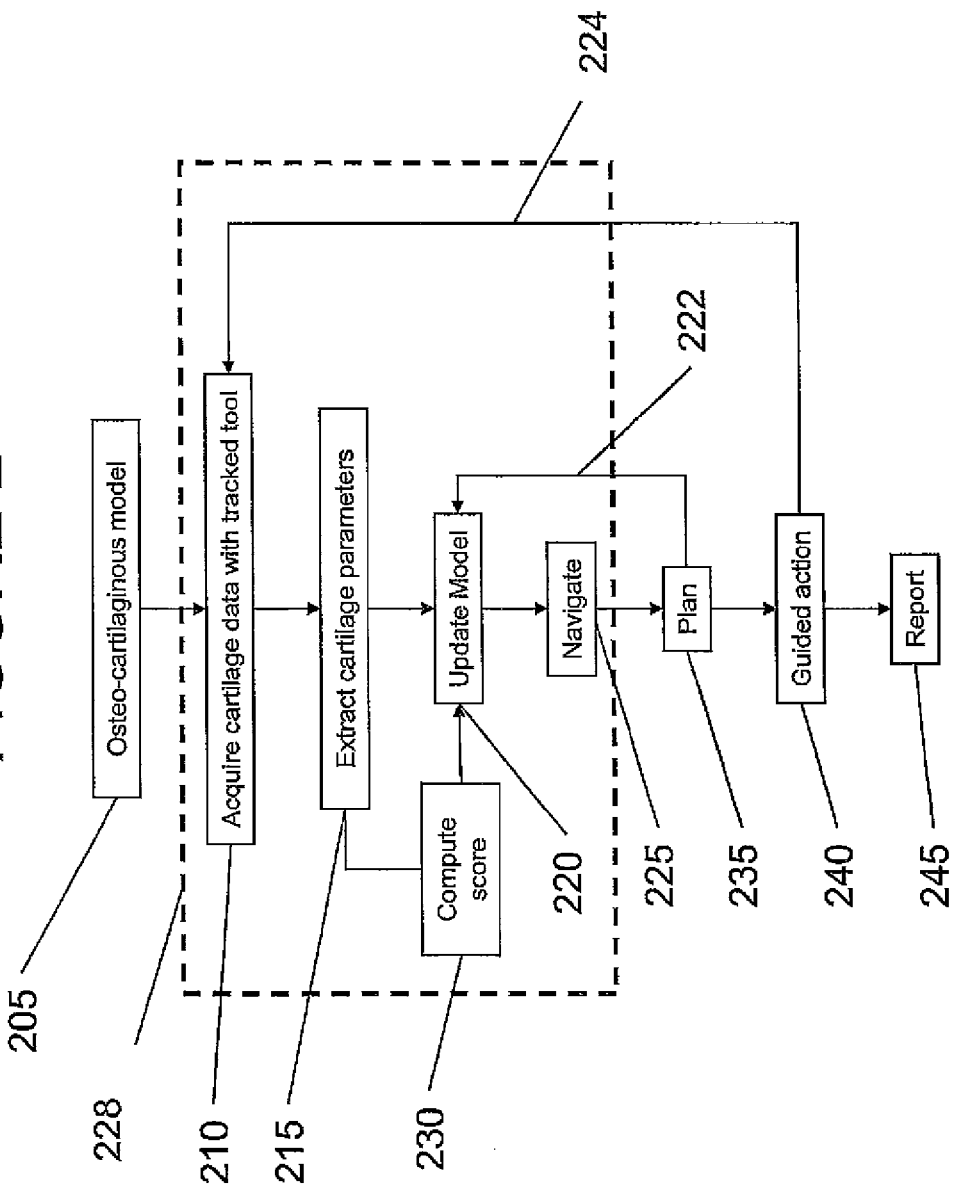
FIG. 2 is a process flow-chart describing one of the embodiments of the present invention.

FIG. 2 illustrates a possible process of the present invention. The entire process includes several features and options for optimizing use of the system in cartilage treatment as will be described below; but in general, the overall method involves providing a 3D osteo-cartilaginous model (step 205), acquiring cartilage data with at least one tracked tool (step 210), extracting at least one parameter that is indicative of the patients cartilage quality (i.e. health) from the cartilage data (step 215), incorporating these parameters into the 3D osteo-cartilaginous model, navigating acquisition and treatment tools and instruments with respect to this model (step 225), and updating the model during the procedure (step 222). An osteo-cartilaginous model is herein defined as a model that includes any cartilage and/or bone data, including the morphology (geometry) of cartilage, cartilage layers, bone and subchondral bone surfaces. The osteo-cartilaginous model may also have biomechanical or biochemical data embedded within.

In a preferred embodiment of the present invention, all these steps may be performed during an arthroscopic procedure. In other words, the steps can be performed in real time as the surgical procedure proceeds in order to provide the surgeon with the best possible information available to assist the surgeon in the procedure and yield superior results.

Tools for Acquiring 3D Cartilage Raw Data and Extracting 3D Multimodal Cartilage Parameters The system 10 contains various tools of different dimensions for acquiring different types of data (step 210) and for extracting various parameters (step 215) to assist cartilage examinations and/or surgical procedures. The system tools described hereafter preferably have the ability of being inserted into the joint and tracked with a position measurement system in order to acquire position registered data of the cartilage (step 210), and they can be provided in different dimensions to suit the type of procedure being preformed (diagnostic or therapeutic). Tools for arthroscopic surgery may be provided with diameters that are small enough to be inserted through a portal (e.g., on the order of ~5 mm or smaller), while tools for examination only can be provided with even smaller sizes (e.g., ~2.5-1 mm or less) so that they can be punctured through the skin and into the joint, not requiring the patient to receive more than a regional or local anesthetic.

Two kinds of tools can be considered: those which can be used during the arthroscopic procedure (pointer, arthroscope, ultrasound probe, Optical Coherence Tomography probe, Infrared probe, Interferometric Laser Imaging System, fluorescent imaging system, others) and those which can be used to generate the provided model and provide additional information (in other words, the data is not acquired during the procedure and these tools include magnetic or X-ray based imaging).

A 3D Tracked Pointer

In one embodiment of the present invention, the system 10 contains a simple pointer 120 with tip 124 and reference body 123 is provided for digitizing points as shown in FIG. 1. Using a calibration process, the relationship between the pointer tip 124 and reference body 123 is known, and therefore the position of the pointer tip 124 relative to the world reference frame 38 and bone 2, 4 is known. The user can thus use the pointer 120 to locate or "digitize" points on the surface of the patient's skin, cartilage, and/or bone. The pointer 120 can be sharp so as to allow puncturing through the skin to acquire points percutaneously.

3D points on the border of a visually identifiable cartilage defect can be acquired to define the spatial location on the 3D localized anatomic model. This is preferably performed under arthroscopic conditions, by inserting the probe 120 into the joint and using an arthroscope (video) to guide the digitization. This could likewise be performed using an ultrasound transducer. A geometrical (shape of the border) and quantitative (depth of the involvement, area defined by the border, volume of the defect, curvature of the palpated surfaces, others) description of the visual defect is therefore extracted from these points. This parameterization can be assisted and even automated using a defect model (such as a simple geometric shape, like a cylinder, ellipse, or spline function) that is morphed to the acquired points.

In the case of visually suspicious pathological cartilage surface areas for which depth and volume are not obvious or available, complementary description of the superficial or subsurface defect can be performed by using image processing tools applied to the images or sequences such as, video, MRI, or ultrasound, of the suspicious cartilage area identified by the pointer 120 (texture characterization of the area defined by the borders palpated points, local curvature, others).

When local cartilaginous tissue characterization is performed over the entire the joint surface, or a substantial portion thereof, global parameters related to the cartilage quality may be extracted using the 3D joint model. For instance, the percentage ratio of total cartilage surface or volume which is healthy vs. pathologic, the cartilage defect surface or volumic distribution, or other measures can be calculated. These parameters can also be computed locally, for example, for a specific region or compartment of the joint (e.g., medial knee compartment). Measures on one region or compartment may be compared with other regions/compartments. This global evaluation of the osteo-cartilaginous tissue, may assist the clinician in making a therapeutic decision.

The remaining tools consist of devices for imaging cartilage for the purposes of acquiring data for which a parameter can be extracted that is indicative of cartilage quality or state of health of the tissue. One common feature of all of these imaging devices is that they are tracked by the position measuring device 50 in the world coordinate system 38 during the acquisition stage (step 210). In addition, each of these tools is calibrated such that the 3D coordinates of the data or image pixels received from the device are known in the coordinate frame of the reference marker associated with the device (e.g., device 152). Knowing the position relationship (i.e. transform) between the tool coordinate frame (device 152) and the pixel data (represented at 155) allows one to determine the position of the pixel data in the world coordinate frame (38), as well as, the coordinate frame of the tracked bone (coordinates 103) (via the tracker 105). Thus any data acquired on the cartilage of bone 2 can be stored and represented in the coordinate frame 103 of the bone, and the relative positions and spatial relationships between the image data are thus maintained. Moreover, cartilage data from multiple devices can be acquired, stored, processed, and visualized in the bone reference frame.

A 3D Tracked Arthroscope

The system preferably includes an arthroscope for direct visualization of the cartilage and bone surfaces and other tissues in the joint. The video signal from the arthroscope can be inputted into the computer and displayed directly on the screen 32, or on an independent monitor. The arthroscope can be a 2D arthroscope or 3D arthroscope (stereoscope) that is tracked relative to the bone with the position measuring system. In one embodiment, arthroscope has an integrated tip that is calibrated and can be directly used to digitize the bone and cartilage surface. As mentioned previously, the tool, in this case an arthroscope can be of a small diameter (e.g., approximately 1-2 mm) that allows insertion into a joint of a patient using only a regional or local anesthetic (see U.S. Pat. No. 6,419,654 entitled Diagnostic Needle Arthroscopy and Lavage System, or US Patent Application Publication No. 2007/0167681) (both of which are hereby incorporated by reference in their entirety).

In another embodiment, the arthroscope is configured to acquire points on the bone/cartilage surface using non-contact techniques, i.e., where the points are determined by analyzing the images generated by the arthroscope. The tracked and calibrated video arthroscope or stereo arthroscope can be used to acquire images of the bone and cartilage surfaces while simultaneously measuring the position of the scope relative to the bone. Imaging processing techniques can be used to extract the coordinates of the surface in the reference frame 103 coupled to the bone. Line, grid or more generally structured light projection techniques can be used where lines/structured light are projected onto the joint surface using laser or other light forms that are detectable in the arthroscope images, and the position of projecting device is measured or known with respect to the scope. The imaged patterns are then segmented from the video images and the 3D coordinates of the projected lines/structures are extracted as surface contours or points. This provides a convenient method for the surgeon to both acquire data on the surface, and to directly visualize it with a single tool.

As introduced previously, the arthroscope can also be used for extraction of cartilage quality characterizing parameters using image processing techniques (such as for instance texture characterization of the viewed region). This 3D image processing may be automated or manual (as for instance by using a virtual pointer to characterize the region of interest on acquired video images). Furthermore, because the arthroscope is calibrated and tracked in the world reference frame, these parameters can be localized on the anatomic model of cartilage and/or bone relative to the studied joint, and tracked vis a vis the 3D real-time image processing.

A 3D Tracked Endoarticular Ultrasound Probe

In a preferred embodiment of the present invention, the system includes an intra-articular ultrasound probe 150 (FIG. 1) that is tracked and is capable of being inserted inside the joint, where the joint contains an aqueous solution with known acoustic properties (i.e., speed-of-sound). The intra-articular ultrasound probe 150 has a tip 153 intended to be inserted into the joint space, and emits ultrasound waves directly onto the cartilage surface in order to image the cartilage (see FIG. 2). The intra-articular ultrasound probe 150 is calibrated such that the relationship between the pixels in the image and the reference body 152 coupled to the probe is known. By tracking the position of the reference body 152 on the probe 150 relative to the bone, the position of the acquired images 155 on the bone is known. If the probe is a linear array, it is capable of acquiring 1D, 2D or 3D data in real-time. If it is a true 2D array, this would require the probe could open up (such as a fan, for instance) in a joint to expose all the transducer elements. The intra-articular ultrasound probe 150 can be a 1D (A mode), 2D (B mode) or 3D probe which is capable of acquiring images along a line (1D), in a plane (2D), or in a volume (3D). There are various known methods to construct 3D image volumes of 3D tracked ultrasound probes using both 2D and 3D arrays in which the transducing elements are arranged in a line or in a 2D matrix, respectively. For further information on calibration, see for instance U.S. Pat. No. 5,447,154 entitled Method for Determining the Position of an Organ, by Cinquin et al. or Mercier et al, "A review of calibration techniques for freehand 3-D ultrasound systems", in Ultrasound in Medicine and Biology, Volume 31, Issue 4, Pages 587-587, each of which is hereby incorporated by reference in its entirety. For further information on the reconstruction of a 3D image volume, see for instance Rohling R et al, "A comparison of freehand three-dimensional ultrasound reconstruction techniques", Medical Image Analysis (1999) volume 3, number 4, pp 339-359.

For a discussion of the basic ultrasound principles and techniques, see Physical Principles of Medical Ultrasonics by (Eds.) C. R. Hill, Jeffrey C. Bamber, G. R. Ter Haar, published by John Wiley and Sons Ltd; 2Rev edition, 2004.

Different cartilage characterizing parameters (215) can be acquired by the ultrasound probe 150 inserted inside the joint.

In one embodiment, the integrated ultrasound probe and system is capable of determining the roughness (i.e. fibrillation) of the cartilage articular surface. Roughness is defined as a measure of the small-scale variations in the height of a surface, and can be measured in various ways (e.g., Average roughness ($R_a$), Root mean square (RMS) roughness, Maximum height, Roughness numbers, as defined by ISO 1302, see http://en.wikipedia.org/wiki/Roughness).

Figure 6:
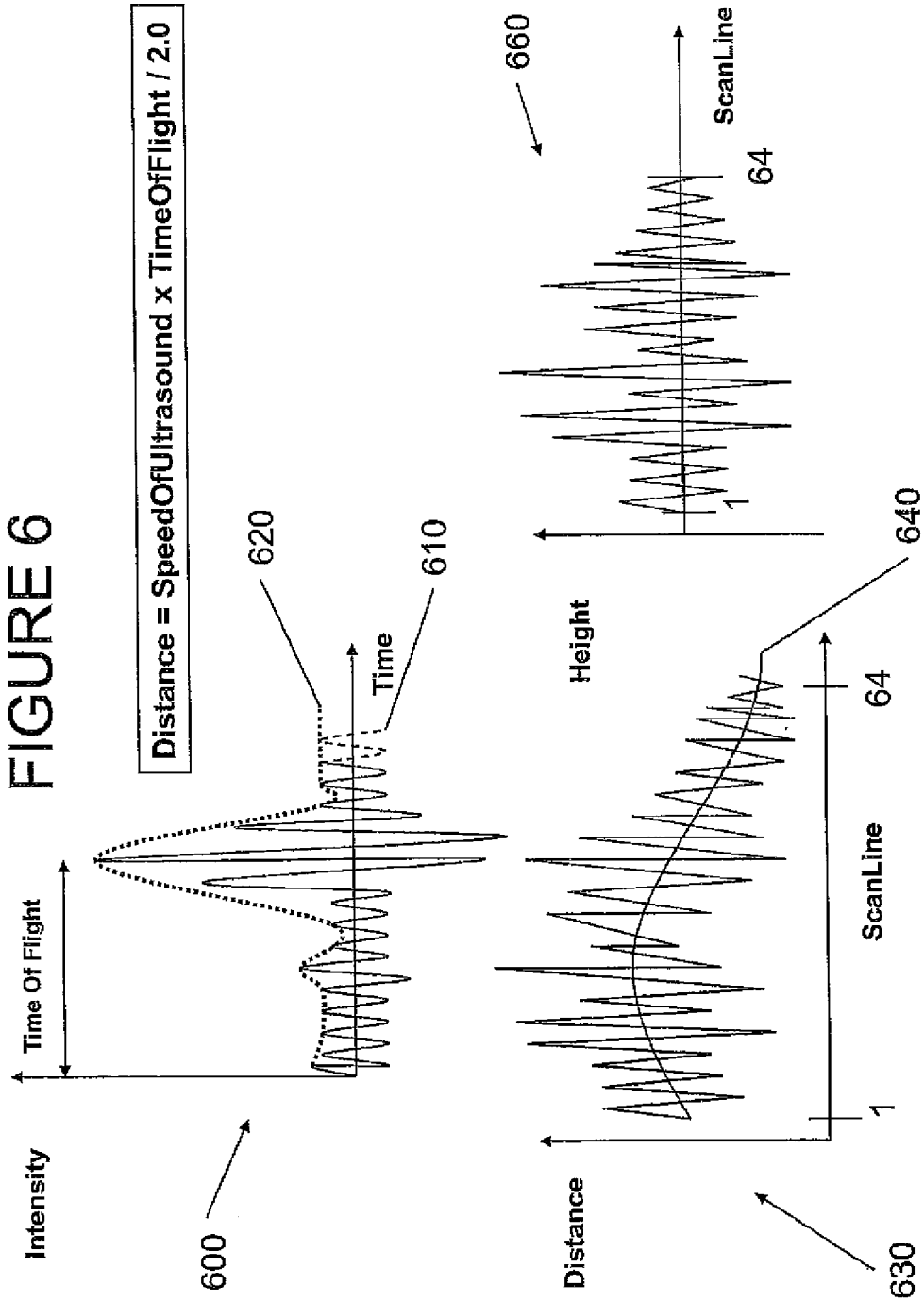
FIG. 6 illustrates a roughness calculation from an ultrasound scan-line.

Disruption of the cartilage surface can result in a change from a normal smooth appearance to a rough or fibrillated appearance. For instance, in osteoarthritis, these fibrillations range from 20 to 150 µm in size. Roughness parameters can be calculated using the data acquired with the ultrasound probe. For instance, roughness at any point of the surface can be computed from the radiofrequency (RF) signal. It can be calculated as the average roughness, as the root mean square roughness, as the maximal height, or as the standard deviation of the distribution of the "distances" between the points in the RF signal corresponding to the water-synovial fluid/transducer interface and that of the water-synovial fluid/cartilage interface. Referring to FIG. 6, for each scan-line, the distance is estimated by the ultrasound flight time (pulse-echo time) information 600 determined on the radio-frequency signal 610. The flight time is determined as the location of the maximum value of the Hilbert transform envelope 620 calculated for the reflected signal. Because the probe is in the joint and the joint is filled with fluid in arthroscopic conditions, the speed of ultrasound may be estimated in an accurate way using the known properties of the fluid (for instance, in pure water, at 20° C., the speed of ultrasound is reported at 1480 m/s). Alternatively, correction factors for the speed of sound can be determined for the various mediums and tissues by calibration. The distance distribution 630 is then estimated from the time of flight and the known speed of sound. The baseline 640 for computing the relative height is estimated by fitting a smooth spline on the data. The relative height distribution may then be computed 660. This distribution is used to characterize the roughness (as for instance, by using the average height or average roughness). For an approach based on standard deviation, see Saarakkala S et al. "Quantitative ultrasound imaging detects degenerative changes in articular cartilage surface and subchondral bone", Phys Med Biol. 2006 Oct. 21; 51(20):5333-46). These distances may also be calculated directly from the image built from the RF signal (e.g., the B-mode image) and after the calibration of the probe. Other methods for characterization of the distance distribution may also be used.

Another possible approach to characterize the roughness of the cartilage surface is to use the angular distribution of the mean backscatter power. The mean backscatter power can be seen as the mean acoustical energy by time unit which is reflected from the cartilage surface. For a very smooth surface, this energy is mainly reflected in one direction (specular reflection). For rough surface, this energy is reflected at a number of angles (diffuse reflection). The determination of the spatial angular distribution thus enables one to estimate the roughness of the surface. This angular distribution can be determined from the radio-frequency signal (see Chiang E H et al, "Quantitative assessment of surface roughness using backscattered ultrasound: the effects of finite surface curvature", Ultrasound Med Biol. 1994; 20(2):123-35).

In addition to roughness, other parameters can also be computed to provide an indication of the quality of the cartilage. From the echo sound record, the transformed wavelet map is computed by using the wavelet transformation. The maximum of the magnitude and the echo-duration can be extracted from the time-frequency plane. The echo duration is defined as the length of time over which 95% of the echo signal is detected. As reported by Koji Hattori et al. in "Quantitative Ultrasound Can Assess Living Human Cartilage", Bone Joint Surg Am. 2006; 88:201-212, these previous parameters are linked to cartilage degeneration (decreased magnitude, prolonged echo duration in case of cartilage degradation).

Other parameters can be estimated during minimally invasive ultrasound intra-articular exploration with high frequency ultrasonic probe (e.g., 50 Mhz). These parameters are computed by quantitative analysis of the radiofrequency signal backscattered by the cartilage, such as, for instance, the thickness, the Integrated Reflection Coefficient (IRC), the Apparent Integrated Backscatter (AIB) (see, Cherin E et al, Evaluation of acoustical parameter sensitivity to age-related and osteoarthritic changes in articular cartilage using 50-MHz ultrasound, Ultrasound Med Biol. 1998 March; 24(3):341-54, or Saarakkala S).

Pathological cartilage vascularization (hyaline cartilage being avascular) can also be estimated by other ultrasound modalities, as for instance by using Doppler techniques—power Doppler, color Doppler, spectral Doppler, directional power Doppler or by using ultrasonic contrast agents (such as, for instance, encapsulated micro-bubbles to evaluate cartilage pathological vascularization).

The ultrasound probe 150 can be also used to assess biomechanical properties of the multilayer osteo-cartilaginous tissue. For instance, new approaches are currently developed to determine 2D stiffness distribution (see Zheng Y P et al, "Ultrasound elastomicroscopy using water jet and osmosis loading: potentials for assessment for articular cartilage", Ultrasonics. 2006 Dec. 22; 44 Suppl 1:e203-9), Young's moduli distribution (see Saarakkala et al, "Mechano-acoustic determination of Young's modulus of articular cartilage", Biorheology. 2004; 41(3-4):167-79)

Other ultrasound imaging techniques methods for enhancing the acquisition of these cartilage characterizing parameters or acquiring new parameters with ultrasound can be used, such as, for instance, tissue harmonic imaging (with or without contrast product), pulse-inversion harmonic imaging, compound imaging, Acoustic Radiation Force Impulse (ARFI) Imaging.

As mentioned previously, the different characterizing parameters can be obtained by the intra-articular ultrasound probe 150 in different modes, such as, 1D ultrasound (for instance, maximum magnitude and echo duration can be obtained by a 1D A mode ultrasound probe in arthroscopic conditions), a 2D arthroscopic ultrasound probe (B imaging mode, Doppler mode, TH mode, Radio Frequency signal from 2D ultrasound rigid probe), or 3D ultrasound probe. In view of the calibration of the probe and its 3D tracking, these cartilage ultrasound parameters are localized in the world reference frame.

The Ultrasound probe 150 can also be used to determine geometrical (shape of the border) and quantitative (depth of the involvement, area defined by the border, volume of the defect, curvature of the scanned surface, etc.) descriptions of the visual defect from points acquired by the calibrated and tracked ultrasound probe and identified on the ultrasound image.

In another embodiment of the present invention, the acquisition of these ultrasound cartilage parameters is assisted and improved using additional information on the location of the ultrasound beam with respect to the osteo-cartilaginous surface. This is described more precisely in the part of this document entitled "morphing, mapping, and visualization of a volumic osteo-cartilaginous model"

A 3D Tracked Calibrated Endoarticular Optical Coherence Tomography Probe

In another embodiment of the present invention, a tracked and calibrated Optical Coherence Tomography probe is used to acquire information on the cartilage. Optical Coherence Tomography (OCT) is a cross-sectional imaging technology that can be used for micro structural imaging of human tissue, including articular cartilage. The OCT image is generated from measuring the back-reflectance of near-infrared light yielding 2D images (for instance, 500×1000 pixels covering an area 6 mm in length and ~3 mm in depth, see Pan Y hereafter) at a high spatial resolution (4-20 micron) that is comparable to low power histology. This tool can therefore be used arthroscopically to evaluate articular cartilage irregularities (a cartilage defect, surface topography, and subsurface architecture) and for the evaluation of cartilage repairs (repair tissue integration). For instance, see Pan Y et al, "Hand-held arthroscopic optical coherence tomography for in vivo high-resolution imaging of articular cartilage", in J Biomed Opt. 2003 October; 8(4):648-54. Different cartilage quality characterizing parameters may thus be defined by using 2D image processing tools applied to OCT images.

In another embodiment of the present invention, a variation of this OCT imaging technique that is based on near-infrared light and is known as Polarization-Sensitive Optical Coherence Tomography (PS-OCT) is used. This enables the assessment of tissue birefringence from which complementary information related to cartilage organization are computed, such as, for instance, collagen organization, collagen angle, collagen type, and the presence of multiple birefringence tissue. In addition, endoscopic OCT and polarization-sensitive OCT can be combined to allow the advantages of both techniques. See, for instance, Mark C. Pierce et al, "Endoscopic polarization-sensitive optical coherence tomography", in Proc. SPIE Vol. 6079, 607928 (Feb. 20, 2006).

For ease of illustration, both the ultrasound probe and the intra-articular (PS)-OCT probe are generally indicated at 150 since the instrument 150 is merely a generic depiction of a tool that can be used in accordance with the present invention. The probe 150 has a tip 153 intended to be inserted into the joint space, and emits near infrared light directly onto the cartilage surface in order to image the cartilage (see FIG. 2). This probe 150 can be calibrated such that the position relationship between the pixels in the OCT image and the reference body 152 coupled to the probe is known. Methods presented for calibrating the ultrasound probe can be used to calibrate the (PS)-OCT probe 150 (for instance, see Mercier et al.). A calibration phantom having material specifically adapted to the specificity of the electromagnetical waves emitted by the OCT probe may be utilized for a more accurate and robust calibration. One approach could consist in using a phantom with multiple crossing wires positioned and sized to be suited for the imaging depth and resolution (depth of study) by OCT (i.e., very thin wires—diameter<0.1 mm—included in a gel with optical properties similar to the tissue being imaged, with an accurate known geometrical description of the positioning of the different wires). From this phantom, the calibration will follow the same steps as for ultrasound calibration. By tracking the position of the reference body 152 on the probe 150 relative to the bone, the position of the acquired images 155 on the bone is known. Thus, each pixel in the OCT image will be localized in the common world reference frame 38.

A 3D Tracked Endoarticular Infrared (IR) Probe

In another aspect of the present invention, a calibrated and tracked IR probe is provided to acquire information and data indicative of the quality of the patient's cartilage. This IR technique is based on the spectroscopic analysis of the reflected light in the mid-near-Infrared domain by using an infrared fiber-optic probe (IFOP). The probe can incorporate a crystal which is in contact with the surface of the cartilage. After emission and reception of IR light, an averaged (smoothed) spectroscopic signal is computed. Automatic analysis is then performed in order to identify the quality of the cartilage by analyzing the peaks of the signal. In particular, the peak at 1338 cm$^{-1}$/amideII has been correlated to the histologic Mankin grade, a histological gold standard used to assess cartilage quality (See for example U.S. Pat. No. 7,167,742 B2 to Camacho et al., entitled "Utilization of an Infrared Probe to Discriminate between Materials" in which IFOP technology is used to recognize materials that have a distinguishable infrared spectrum (such as bone/cartilage, and West P A et al, "Fourier transform infrared spectral analysis of degenerative cartilage: an infrared fiber optic probe and imaging study", Appl Spectrosc. 2004 April; 58(4):376-81 in which degraded tissue exhibit increased amide II (1590-1480 cm$^{-1}$)/1338 cm$^{-1}$ area ratio). IMP technology is currently a 1D probe (though 2D and 3D probes could be incorporated). To localize in the world reference frame 38, the cartilage parameters acquired by a 1D probe, it is necessary to know, in real-time and in this frame, the 3D position of the IFOP tip. A similar methodology that has been described for the pointer calibration can be used, in which a tracker is attached and the probe and the position of the tip is calibrated with respect the marker coordinate frame.

A Tracked Endoarticular Interferometric Non-Destructive Laser Imaging System

Figure 7:
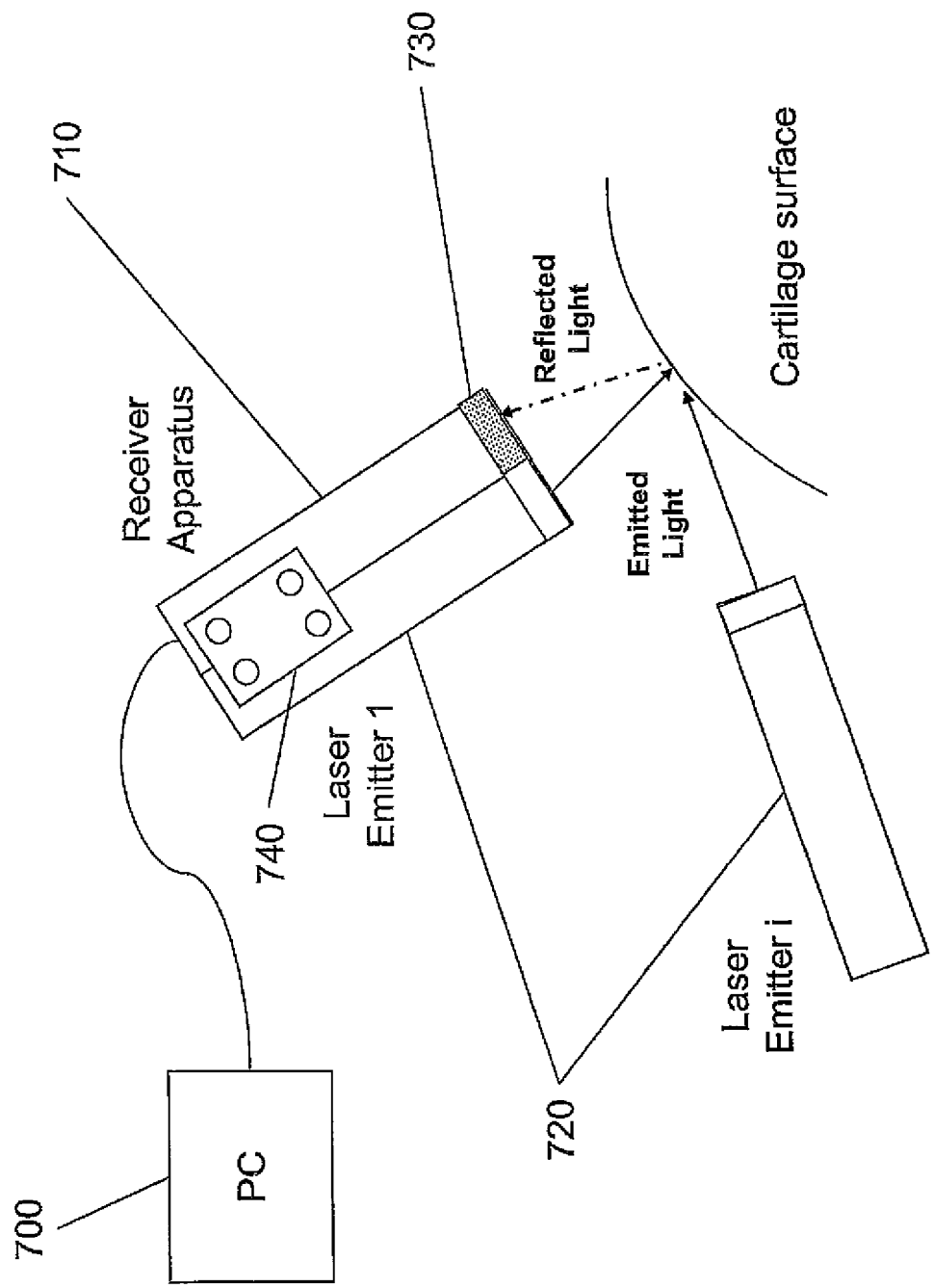
FIG. 7 is a schematic view of a tracked interferometric non-destructive laser imaging system.

In another aspect of the present invention, a calibrated and tracked 3D interferometric laser imaging probe is provided, along with a method for cartilage assessment that is based on digital shearography. Referring now to FIG. 7, this apparatus includes:

a—one or more sources 720 of coherent or partly coherent light, for radiating light directly on the cartilage surface,
b—one or more radiation receiving apparatus 710 for receiving light reflected by the source,
c—a system for applying a stress to the cartilage tissue (not shown), and
d—a computer system 700.

With respect to element a (source 720)—A coherent or partly coherent light shines directly on the cartilage surface with the light being reflected from the cartilage surface. The source of coherent or partly coherent light can be inside or outside the studied joint.

In one embodiment of the present invention, the light source is positioned inside the joint, by, for example, using a water proof laser diode housed in the probe tip. This source can be connected to an expanding lens.

In another embodiment of the present invention, the light source is positioned outside the joint and an optical relay is used to conduct the light from the source into the joint to shine on the cartilage surface. Different optical relays can be used (such as, for instance, armored single-mode optical fiber, borescope, polarization maintaining optical fiber, etc.). An expanding lens can be connected to the optical relay.

Contrary to a mirror which is a specular reflective surface, the cartilage surface is a diffuse reflective surface, and more so when the surface is degenerated from disease (cartilage roughness has been demonstrated to degrade with OA). When a diffuse reflective surface is illuminated with laser light, a speckle pattern is visible, which is not the case with specular reflective surfaces. The speckle pattern can thus be analyzed to help assess the cartilage surface quality.

With respect to element b (receiving apparatus 710), a reflected light receiving apparatus is used for receiving the light directly from the cartilage surface when the cartilage surface is in a stressed and/or in an unstressed condition. This apparatus can be inside the joint, or outside the joint with an optical relay to conduct the light from the probe tip to the light receiver. It can include a shearing device. A shearing device is used to create an interference pattern in the light detector by making interact two beams B1 and B2 in the light detector. B1 is the reference beam. B2 is the "sheared" beam. B2 is made of rays backscattered from points of the cartilage surface. These points are neighbors of points of the cartilage surface, from which the rays backscattered produce B1. Different shearing devices exist, such as, for instance, a Michelson shearing interferometer, a double refractive prism, or other known shearing devices. The reflected light receiving apparatus may also include a variable wave retarder. This device is an optical device enabling to create a phase retardation in the phase of the incident beam (phase retardation of π/4, π/2, etc.). This device may be a part of a modified Michelson shearing interferometer. It also may be a liquid crystal (see for instance Hung et al, "Shearography: An optical measurement technique and applications", Materials Science and Engineering R 49, 2005, 61-87). In particularly, variable wave retarder is used in different shearographic techniques (time-shifting technique) to exactly calculate the phase in a set of interference pattern characterized by known phase retardation (see "Digital Shearography. Theory and Application of Digital Speckle. Pattern Shearing Interferometry", from Steinchein et al.). Combinations of the different approaches are possible. One of the outputs of the receiving light apparatus is a digital speckle pattern image.

As with the light source the light receiving apparatus is preferably positioned inside the joint. It consists of a water proof micro charge-coupled device (CCD) camera (volume<5 mm$^3$) with a frame grabber. A shearing device is fixed in front of the camera (biprism, for instance). This apparatus will thus record a "modified" speckle pattern reflected from the cartilage surface that is illuminated with the laser light. Images are recorded at a frame rate and transmitted to the computer. Similar to the light source, the light receiving apparatus can also include an optical relay that conducts the "natural" speckle pattern to an associated recording apparatus, for instance, a variable wave retarder made of liquid crystal and a shearing device, fixed in front of a CCD camera. This latter is connected to a computer.

With respect to element c, different cartilage stressing systems can be used to apply a load to the cartilage to determine the cartilage stiffness. Mechanical forces can be applied on the surface cartilage using an arthroscopic indentation instrument. Load can also be applied by water jet stream. A system based on ultrasound (20 Khz-200 Mhz) can also be used to apply a load. This stressing system may be made of multiple ultrasound elements, having either uniform or differing characteristics that can be activated in parallel or sequentially. By putting the stressing system inside the joint, different stress schemes or patterns may be applied on the cartilage surface, as for instance, by using different acoustical waves, focused at different depths, with different frequency schemes (variation of ultrasound stress frequency, others). Under static or dynamic stress, the cartilage surface will deform in a different way according to the flaw inside the cartilage tissue. From these non-uniform deformations, the reflected speckle pattern is thus modified in a different way.

With respect to element d, the computer is preferably a separate computer that is dedicated to the control of the interferometric non-destructive laser imaging system, and that is connected to the main computer 30 of the navigation system 10 (it could however be the same computer). The computer system is used to synchronize the different elements (image acquisition, the applied test sequence, the computer-controlled variable wave retarder, etc.), for programming different testing sequences, for recording the different data, for displaying, in real time or not the digital reflected speckle pattern images, for the analysis of the different digital reflected speckle pattern images. This analysis may take into account at least one reflected speckle image without stress. Different known algorithms have been developed to identify potential flaws inside the studied surface by analysis of reflected speckle pattern.

In a preferred embodiment of the invention, and in relation with the experimental arthroscopic conditions, a water proof laser diode is fixed rigidly to a water proof Charge-Coupled Device (CCD) camera. The water proof camera is focused on the cartilage region of interest and a shearing device is fixed in front of the lens (biprism). The set (laser diode+camera) is maintained in a fixed intra-articular position relatively to the cartilage surface by, for instance, a light endoscope holder robot. Two successive pictures are recorded by the system. The first one is performed without load. The second one is performed with a load applied by a water jet. The spatial phase shifting technique is applied to compute the phase distribution on each recorded interferogram image. The phase map of the relative phase change is obtained by digital difference between the two images. This phase map, displayed on the screen of the computer, enables the direct visualization of potential flaws inside the cartilage surface.

For more information on the principles and details of operation of interferometric laser imaging systems see the following documents: U.S. Pat. No. 6,934,018 B2 from Shaw et al., entitled "Tire Inspection Apparatus and Method"; U.S. Pat. No. 6,246,483 from Smith et al., entitled "Apparatus and Method for Shearographic Inspection and Non Destructive Testing of Articles in a Vacuum Chamber", in which an apparatus is reported for inspecting or testing a sample using shearographic techniques; US Patent Application Publication No. 2007/0121121 A1, from Whilhem et al., entitled "Method and Apparatus for Determining the Deformation of Objects", in which a method and apparatus are described for studying object deformations based on shearography. U.S. Pat. No. 4,655,302, entitled "Interferometric Eye Test Method and Apparatus", Grant et al. which describes an ophthalmologic test apparatus employing interferometric holography and shearography. Information on the principles and application of shearography can be found in the book by Steinchein et al, entitled "Digital Shearography. Theory and Application of Digital Speckle. Pattern Shearing Interferometry", ed. SPIE press (2003).

One of the main disadvantages of the prior-art techniques is the methods in which a load is applied on the material to obtain the desired stress conditions (e.g. vacuum chambers) and in which the interferometric data is acquired (not compatible with clinical conditions).

In another embodiment of the invention, the set-up is the same as described previously, but the load is applied by an ultrasonic device, at difference frequencies. For each frequency, in a steady state vibration, a stress image is recorded. By using techniques related to time integrated shearography, interferograms with visible fringe patterns may be displayed, enabling the direct visualization of potential flaws inside the cartilage surface.

As mentioned previously, the 3D endoarticular interferometric non-destructive laser imaging system is calibrated, tracked 740 and navigated. By calibration of the CCD camera with the shearing device according to a perspective model (ideal pinhole camera), each pixel of the image is related to a unique incident ray (for complementary information related to camera model and calibration, see, for instance, the book "Three-Dimensional Computer Vision—A Geometric Viewpoint", by O. Faugeras, The MIT Press, Cambridge, Mass., USA, 1993). The camera is rigidly linked to markers that enable the position measurement system to track the tool relative to the bone. Using the transformation determined during the calibration step, we can determine the 3D position in the common world reference frame of the unique incident ray associated to the pixel. In the virtual 3D environment implemented in the computer system which includes a 3D reconstruction of the cartilage/bone in the common world reference frame, the surfacic/volumic representation of the acquired interferometric cartilage data can be calculated from the intersection of the "illumination cone" with the 3D pre-built osteo-cartilaginous model. The cartilage data extracted from interferometric non-destructive laser imaging probe can therefore be presented to the surgeon on the 3D osteo-cartilaginous model.

A 3D Tracked Endoarticular Fluorescent Imaging System

Figure 5:
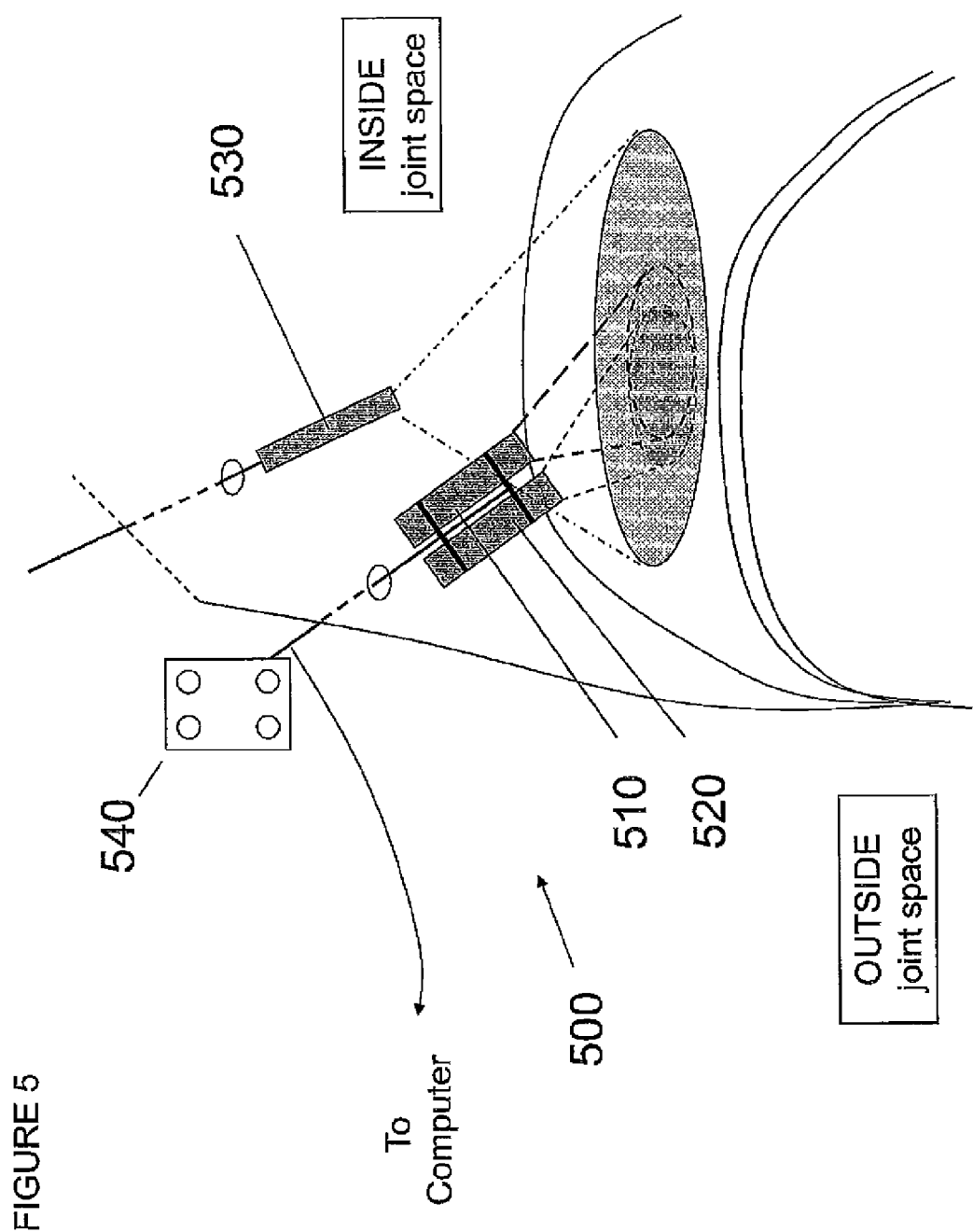
FIG. 5 is a perspective view of a stereoscopic system of the present invention.

Referring now to FIG. 5, another aspect of the present invention is illustrated, where a calibrated and tracked fluorescent imaging device 500 is provided, along with a method to acquire new data on cartilaginous tissue during arthroscopic procedures.

Fluorochrome or fluorophore are commonly used in clinical practice. For instance the fluoresceine (or its derivative), which is a complex chemical substance emitting a reflected fluorescence light when excited under UV, is currently used for ocular angiography. Furthermore, bioengineering methods enable to build fluorescent biological probes (i.e. substances, such as DNA, that are radioactively labeled or otherwise marked and used to detect or identify another substance in a sample) which may specifically link to a particular target, such as fluorescent antibodies. For an overview on fluorescent probes, see "Principles of Fluorescence Spectroscopy" from Lakowicz J., Second Edition, Springer, 2004.

Cytokines are recognized as playing a key role in some cartilage diseases. In the case of osteoarthritis, studies in vitro and in vivo have established that interleukin-1 (IL-1) and tumour necrosis factor (TNF)-$\alpha$ are the predominant pro-inflammatory and catabolic cytokines involved in the initiation and progression of articular cartilage destruction (see Goldring M, "Anticytokine therapy for osteoarthritis. Expert Opinion on Biological Therapy", September 2001, Vol. 1, No. 5, Pages 817-829). Intra-articular anticytokine therapy based on this rationale are now currently evaluated (as, for instance, by intra-articular injection of IL-1 Beta antagonist. See Chevalier X et al, "Targeted anti-cytokine therapies for osteoarthritis" in Bull Acad Natl Med. 2006 October; 190(7):1411-20; discussion 1420, 1475-7). The general aim is to study of the role of cytokines in cartilage diseases, and the unbalance created by these molecules between healthy and not healthy cartilage. As explained more precisely in the following paragraphs, two biochemical factors may be taken into account to characterize this unbalance: cytokine (ligand) and cytokine target (receptor).

Cytokine target (receptor): specific antagonists or inhibitors have been demonstrated to slow disease progression in animal models of cartilage disease (osteoarthritis) and are now clinically evaluated (for instance, IL-1 Beta antagonist). By bioengineering methods, such specific antagonists or inhibitors can be marked by a fluorochrome or fluorophore. Injected in the joint, these marked specific antagonists diffuse into cartilage tissue and interact with their specific target. After a certain time enabling the interaction, the joint is then rinsed out to eliminate the marked specific antagonists which are not linked to receptors on or inside the cartilage surface. Only linked marked specific antagonists remain thus on or inside the cartilage surface ready for the examination.

Cytokine (ligand): current antibodies are already existing and used to target such cytokines. For instance, anti TNF antibodies are used as a therapy in rheumatoid arthritis. Anti TNF alpha therapy has also recently been tested in isolated cases of digital or knee therapy (see Chevalier X et al.). Similar to IL-1 Beta antagonist, TNF antibodies may be marked by a fluorochrome/fluorophore. After a certain time enabling the interaction, the joint is rinsed out and thus only linked marked specific antibodies remain at/inside the cartilage surface.

Other fluorescent probes for other cartilage targets are currently in development, which may be used to study cartilage. For instance, see the article from Krahn et al, entitled "Fluorescently labeled collagen binding proteins allow specific visualization of collagen in tissues and live cell culture", Analytical Biochemistry 350 (2006) 177-185, in which the authors report on the development of new fluorescent probes that are specific to certain types of collagen and small enough to diffuse into tissue.

The present invention uses marked molecules that are detected by an arthroscopic unit, consisting of at least one intra-articular illumination device (530) capable of emitting light at the adapted frequency (for instance, for fluorescein, a light emitting diode (LED) or a laser diodes (LD) centered on the 488 nm excitation peak) and, at least, one intra-articular detector (510) suitable for detecting the reflected fluorescence light (as for instance, a micro CCD sensor with detection centered on the 532 nm emission peak). Furthermore, the quality of the detection of the reflected fluorescence light in the image may be improved by measuring and subtracting the background noise. For instance, see international patent application, No. PCT/FR2006/000131 or WO/2006/087437, from Peltie P, entitled "fluorescence imaging device with two wavelength emission", in which a new apparatus is described, comprising a first light source at a first wavelength corresponding to an excitation wavelength of a fluorophore, a second light source having a second wavelength to record background noise, and a camera. The camera comprises a filter opaque to the first and second wavelengths (to prevent imaging of the excitation light) and transparent to the emission wavelength (allows imaging of the emitting signal). The light sources and the camera are synchronized for alternately activating one of the light sources and enabling the camera to alternately acquire a fluorescence image and a background noise image. By combination of the different (digital) images, the detection of the fluorescent emitted light is improved.

Different methods may be used to localize in 3D fluorescent information acquired by an arthroscopic device based on the above described arthroscopic unit. For instance, the intersection of registered osteo-cartilaginous model and the calibrated and 2D arthroscope images can be used, as previously described with the laser imaging system. Alternatively, the following device can be used: two mini CCD sensors that are rigidly linked together to enable a stereoscopic view of the cartilage surface, used inside the joint and are capable of detecting the reflected fluorescence in an image. The scene is illuminated by at least one illumination source (LED)—ideally two, for background noise acquisition. The stereoscopic system is calibrated such that the 3D coordinates of the viewed fluorescent information can be computed in the referential of the sensors. The whole system, used inside the joint, is also rigidly linked to markers (540) outside the joints. From a calibration step, the 3D coordinates of the fluorescent information are thus determined in the common world reference frame 38, and in the frame 103 of the bone.

The analysis of the 3D fluorescent images enables the determination of new parameters which can be mapped to the Osteo-cartilaginous model to help the surgeon in assessing cartilage quality. One example parameter that can be mapped is fluorescent metabolic information at the cartilage surface as imaged with detector device 510.

Magnetic Resonate Imaging and Magnetic Resonance Spectroscopy

Another approach that is commonly used to study cartilage is to use Magnetic Resonance Imaging (MRI). Different sequences, such as those reported in U.S. Pat. No. 7,184,814 B2 US are currently used to access relevant imaging. These evaluation modalities enable not only the analysis of cartilage but also bone and more specifically the subchondral bone (bone integrity, bone edema). This structural support of the cartilage may have to be taken into account during the cartilage procedure. Because of the 3D acquisition, cartilage/bone quality characterizing parameters (for instance, MRI cartilage thickness, volumic distribution of bone edema, bone structure, biochemical structure, integrity of the collagen matrix, regions of proteoglycan loss, others), extracted from these data by imaging processing tools, are already localized on the MRI model. MRI is typically performed before the arthroscopic procedure, and the MRI data may be used during the surgery, by loading the MRI data on the computer and registering the scan to the bone (see Rigid Model section below). MRI can also be acquired during the procedure and transferred directly to the computer if an intra-operative MRI is available, though this is currently expensive and less common.

3D Registered X-Ray, Computer Tomography Scan, Bone Densitometry

An approach currently used to assess bone quality is X-ray, CT scan, and/or Bone densitometry. Such approaches could be used to assess bone not only in an over-all way, but also to assess subchondral bone (e.g., bone organization—cortical bone, trabecular bone—Macro structural architecture, microstructural architecture, bone geometry, others) in the region of interest. X-ray machines can be calibrated and the images can be registered to the bone and navigated on as is commonly known in the art (see for example U.S. Pat. No. 6,697,664 be Kienzle et al.).

These different quantitative parameters may be taken into account to classify the cartilage defect, according to current (or future) cartilage lesion classification schemes reported in the literature (outerbridge, modified outerbridge, IRCS scale).

Morphing, Mapping, and Visualization of a Volumic Anatomic Osteo-Cartilaginous Model Incorporating 3D Multimodal Cartilage Parameters Referring now back to FIG. 2, which illustrates one possible process for carrying out the current invention. For the purposes of visualization, interpretation, planning, and navigation of the various tools and imaging devices, an osteo-cartilaginous model 205 of a bone is provided. This model can be rigid or deformable as described below.

Rigid Model

In the present invention, a 3D model of the bone and in particular of the cartilage surfaces of the joint are to be registered to the patient's bone and cartilage surfaces during the procedure. In cases when a pre-operative scan 70 or reconstructed scan with model is obtained from CT, MRI, bi-planar X-ray, or another imaging modality, this model can be entered into the system and registered to the patient using data acquired at the time of examination or surgery with the CAOS system 10. Techniques for registering a model to a bone are well known.

For example, one potential approach is described in "Intensity-Based Registration of Freehand 3D Ultrasound and CT-scan Images of the Kidney" by Leroy A et al, published in June 2007 in International Journal of Computer Assisted Radiology and Surgery, in which a pre-operative Computed-Tomography volume is registered to a sparse set of intra-operative Ultrasound Slices or "Registration of Freehand 3D Ultrasound and Magnetic Resonance Liver Images" by Penney G and all, published in: Medical Image Analysis, Volume 8, Issue 1, March 2004, Pages 81-91, in which a pre-operative MR volume is registered to a sparse set of intraoperative ultrasound slices. Furthermore, see "Automatic Segmentation of Cartilage in MR Images using CDCG: Chessboard Directional Compensated GVF Snakes" from Ying Chi and all, published in: Proceedings of the International Conference on Medical Information Visualisation—BioMedical Visualisation (MediVis'06), 5-7 Jul. 2006, in which a new fast algorithm is described for accurate segmentation of knee cartilage in magnetic resonance (MR) images. A method for registering a 3D model of the cartilage surfaces of the joint to the patient's bone and cartilage surfaces may be carried out according to the following process: MR cartilage data are acquired before the cartilage procedure. During the cartilage procedure, images of the patient's cartilage and bone data are acquired by a 3D freehand ultrasound probe. By using the intensity based matching method described by Penney G or Leroy A, the MR cartilage data are registered on ultrasound images, i.e. to current patient's cartilage and bone data. The cartilage model which can be multilayered and can be built by automated segmentation of cartilage structures on MR data using the method described by Ying Chi, is then registered to the patient's bone and cartilage surfaces (as "pre-procedure" MR data are registered on "intra-procedure" ultrasound images). A point or surface based matching method can also be employed instead of an intensity based one. In a point or surface based matching procedure, both the pre-operative and per-operative image data are segmented into points, lines or surfaces, and these geometric datasets are matched, typically using an iterative algorithm such as the Iterative Closest Point (ICP) technique. Any combination of intensity or surface based matching could be employed.

Deformable Model

In cases when a pre-operative scan is not available, a deformable or statistical model is preferably registered to the joint using deformation and warping techniques, thus enabling the creation of a complete 3D model of the joint surface without pre-operative data and only data acquired in the operating room. This is described below in greater detail.

In one embodiment of the present invention, the system is capable of generating a 3D model of the patient's joint under examination, without any pre-operative or previously acquired scans. 3D geometrical surface or volumetric models of the bone and cartilage are provided by adjusting a deformable model of the bone to data acquired on the cartilage and bone surface. Examples of some known methods of deforming surface models of a bone to different data sources can be found in the following references: (1) S. Lavallé, R. Szeliski, and L. Brunie. Anatomy based registration of 3-d medical images, range images, x-ray projections, and 3-D models using octree splines. In R. Taylor, S. Lavallé, G. Burdea, and R. Moesges, editors, Computer Integrated Surgery, pages 115-143. MIT Press, 1995 (2) Lavallee S. Bittar E. Szeliski R. Elastic registration and inference using oct-tree splines. In Brain Warping, Toga ed., Chapter 16, pp 283-296. Academic Press 1999. (3) "Building a complete surface model from sparse data using statistical shape models: application to computer assisted knee surgery" by M. Fleute and S. Lavallé, published in Medical Image Computing And Computer-Assisted Intervention—MICCAI'98, Springer-Verlag LNCS Series, pages 880-887, October 1998; (4) Fleute M, Lavallee S, Julliard R. Incorporating a statistically based shape model into a system for computer-assisted anterior cruciate ligament surgery. Medical Image Analysis. 1999 September; 3(3):209-22. (5) Fleute M Shape Reconstruction for Computer Assisted Surgery based on Non-Rigid Registration of Statistical Models with Intra-Operative Point Data and X-ray Images. PhD thesis, University Joseph Fourier, October 2001. However, other known methods of deforming models exist. Each of the above listed references is hereby incorporated by reference in its entirety.

In particular, the three dimensional shapes of the involved bones may be provided with bone morphing techniques, which are capable of extrapolating very few range data to obtain a complete surface representation of an anatomical structure (e.g., a bone). The specific details of some methods for carrying out bone morphing are set forth in the above references but in general, a complete surface model is built from sparse patient data using shape models such as a statistical model. The model can be built from a population of a number of specimen (points), such as femur or tibia points that are digitized. Data sets are registered together using an elastic registration method (e.g., the Lavallee and Szeliski method) based on octree-splines. Principal component analysis (PCA) is performed on a field of surface deformation vectors. Fitting this statistical model to a few points is performed by non-linear optimization. Results can thus be presented for both simulated and real data. This method is very flexible and can be applied to any structures for which the shape is stable.

Cartilage Histological Model

Figure 3:
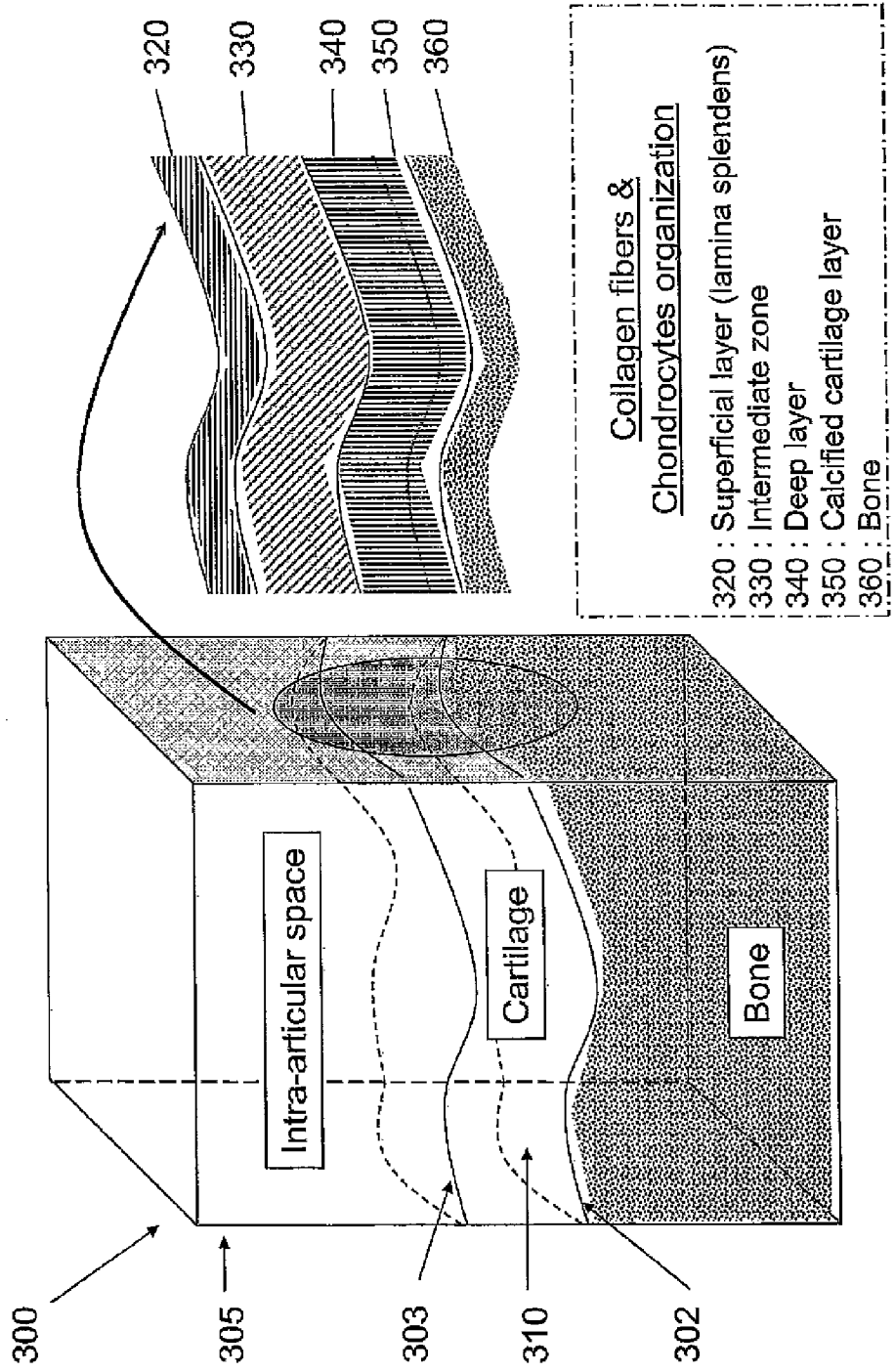
FIG. 3 is a schematic view of an image volume of cartilage.

Referring now to FIG. 3, a schematic view of cartilage morphology is shown. Five (5) layers can be histologically identified inside the osteo-cartilaginous tissue. From the synovial fluid/cartilage interface 303 to the cartilage/bone interface 302, these layers are respectively, the lamina splendens 320, the intermediate zone 330, the deep layer 340, the calcified cartilage layer 350 and the bone 360. To optimally resist the constraints and forces applied to the osteo-cartilaginous tissue, the main components (chondrocytes organization, collagen fibers) are oriented perpendicular to the bone, bending at the transitional zone and flattening at the superficial zone.

In the simplest embodiment of the present invention, the 3D model of the patient's joint consists of at least one 3D osteo-cartilaginous model of at least one bone that is involved in the procedure, this model incorporating at least a portion if not the entirety of the external surface of the cartilage (i.e., surfacic model of the water or synovial fluid/cartilage interface, 303). Preferably, the model is a more detailed multi-layer model that contains at least one additional surface layer, this additional surface layer corresponding to the cartilage/bone interface 302. Further still, this double layer osteo-cartilaginous model may be improved in order to take into account all the anatomic histologic cartilage layers (5 layers previously cited).

Morphing, Mapping, and Visualization

Figure 4:
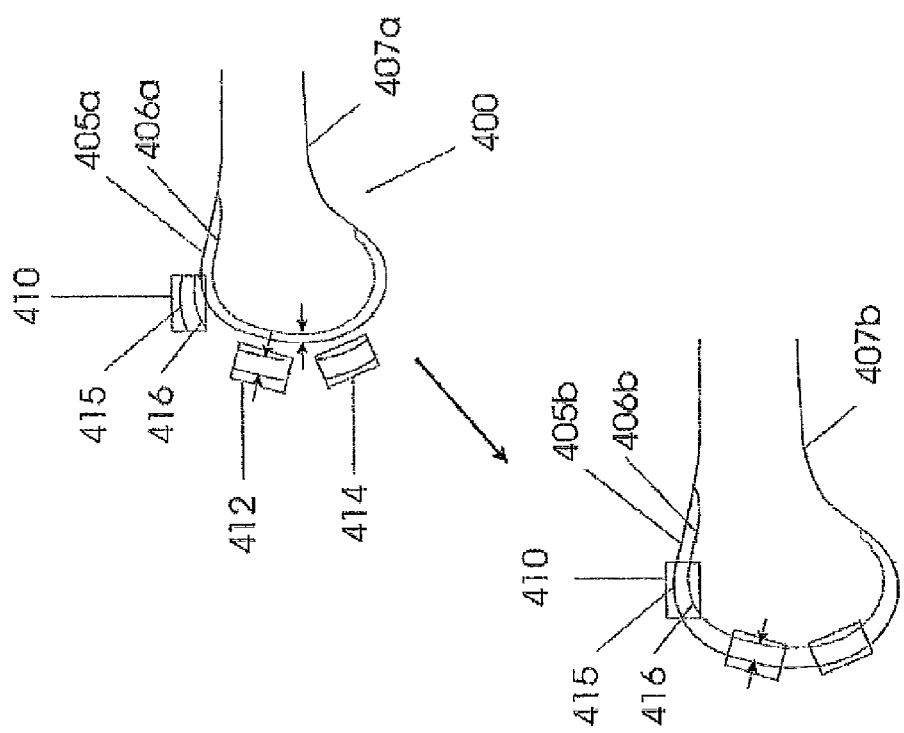
FIG. 4 is a plane representation view of a model of a distal femur that is deformed to acquired image data.

Retelling now to FIG. 4, a deformable double-layer model of a femur 400 having an outer 405a and inner 406a cartilage surface and an external bone surface 407a is illustrated (for the purposes of clarity, the 3D model is illustrated in 2D). This model may have already undergone a initialization process (initial attitude) in which the model is roughly aligned and scaled to the patients bone using a relatively small amount of data that can be quickly and easily acquired (for example, a few landmark points or images acquired in predefined regions, such as the posterior condyles, knee center, kinematically determined hip center, etc.). This initialization data can also be used to establish the bone coordinate system 103, and can be considered to be part of step 205 in the overall process illustrated in FIG. 2. Images of the cartilage (410, 412, 414) are then acquired (210) with at least one of the tracked and possibly navigated imaging tools described previously (for example, with the intra-articular ultrasound probe 150). The acquired images are then segmented such that the external cartilage surface 415 (i.e., the water/cartilage interface 303) and the internal cartilage surface 416 (i.e., the cartilage/bone interface 302) is identified. As the probe has been calibrated beforehand and tracked during the acquisition, the position of these segmented contours (or surfaces in the case of 3D ultrasound) are known in the bone coordinate system 103. Additional cartilage parameters such as surface roughness, maximum magnitude, etc., can also be extracted from the images at this step 215. The model 400, is then deformed or warped using volumetric deformation techniques (for example, the octree-spline or PCA technique described above) such that the external cartilage surface 405a is deformed to 405b, and the internal cartilage surface 406a is deformed to 406b, so that they best match the external 415 and internal 416 cartilage surfaces identified in the images (410, 412, 414). The cartilage thickness at any point in the images or on the model can be calculated (arrows) and mapped on the screen. The warping process and image segmentation process may be interdependent and iterative, and semi- or preferably fully-automatic. As mentioned previously, the deformation process used is an intelligent one that can interpolate and extrapolate between and around the acquired data such that even in areas where no data have been acquired, the shape of the deformed model still reflects that of a realistic bone. However, colors or shading can be used to indicate where the model is most reliable. Cartilage parameters such as roughness are now incorporated into the morphed model (step 220), by assigning a roughness value to each node of the model (parameters can also be expressed as a fraction of a facet of the model surface mesh if a greater resolution is desired). Volumetric parameters of the cartilage quality (such as, internal material flaws as determined by the interferometric non-destructive laser imaging system) can also be presented in cross-sectional images of the model. These representations may be visualized for any part or section of the model in real time, by using the probe to point to any point on the cartilage, and calculating and rendering the cardinal planes intersecting at that point on the screen 32. Visualization of parameters may also be realized with color maps, transparency, or image fusion techniques where at least two different types of images or data-sets are overlapped in a multimodal environment.

Steps 210, 215, 220, and 225 are preferably performed in a continuous real-time loop 228, guided by a single page displayed on the navigation system screen 32. Cartilage quality and surface data can be acquired and extracted simultaneously and mapped/morphed to the model in real-time. The screen displays the Osteo-cartilaginous model with mapped parameters as they are extracted, as well as the position of the probe relative to the model in real time. Thus the surgeon can assess on-the-fly if they have acquired enough cartilage data and if they need to move the probe and acquire additional data in any particular area. To guide the acquisition, the model preferably highlights regions where sufficient and/or not enough data has been acquired making the global acquisition phase fast and intuitive.

Quantitative Quality Score or Quantification-Based Qualitative Quality Score

In a preferred embodiment of the present invention, a synthetic cartilage quality score is computed. This score is a function of at least two different parameters that are available during the arthroscopic procedure. These parameters may be determined before (for example from a pre-op MRI) as well as during the procedure. Several different types of quality scores may be computed, and made available to the surgeon during the arthroscopic procedure. This provides important information for the therapist as he/she can use the score to help plan the appropriate treatment required, and to recalculate the score during or after treatment in order to assess, control, and improve, if necessary the treatment.

Figure 9:
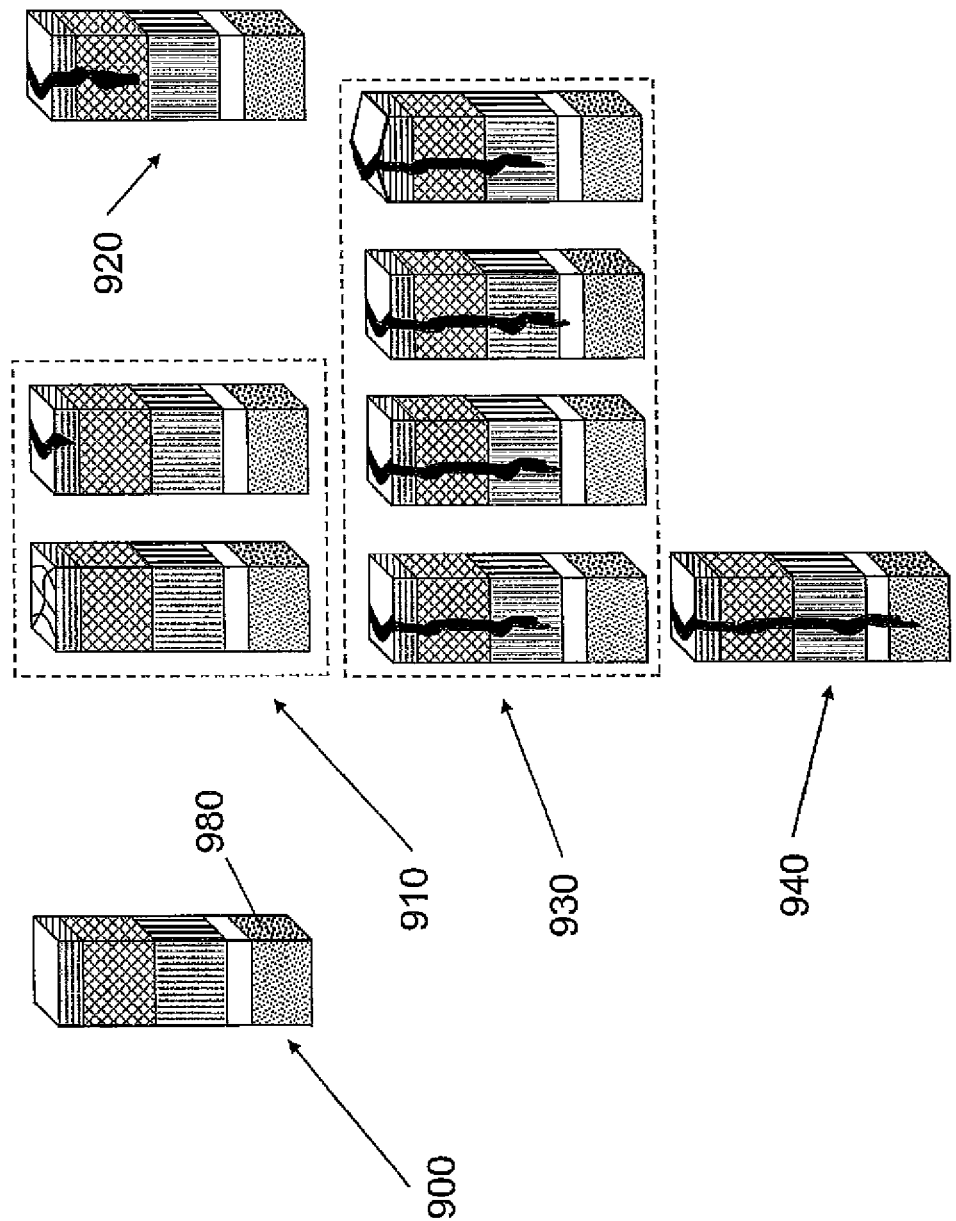
FIG. 9 is a cartilage lesion classification diagram.

Referring now to FIG. 9, a cartilage lesion classification diagram is shown. Cartilage lesions are currently evaluated under arthroscopic procedures by using the I.C.R.S. Hyaline Cartilage Lesion Classification System, suggested at the consensus conference of the ICRS I (international Cartilage Repair Society) in 2002 (see "Evaluation of Cartilage Injuries and Repair", from Brittberg et al, published in the Journal of Bone & Joint surgery). Five grades are described as follows: ICRS grade 0 (normal—900), ICRS grade 1 (nearly normal, superficial lesions with soft indentation and/or superficial fissures and cracks—910), ICRS grade 2 (abnormal, lesions extending down to <50% of cartilage depth—920), ICRS grade 3 (severely abnormal, cartilage defects extending down >50% of cartilage depth—930) and ICRS grade 4 (severely abnormal, complete defect—940) with bone (980) breaking. Nevertheless, this cartilage evaluation suffers from the lack of objective quantification to determine, in an accurate way, when and how to switch between the different grades. One feature of the current invention is to introduce a quantitative evaluation inside the I.C.R.S. Hyaline Cartilage Lesion Classification System, to improve the reproducibility of the classification, especially for very early evaluation.

As has been previously described, the roughness parameter enables early evaluation of cartilage disease. For each point of the cartilage surface for which no obvious lesion is seen, the normality of the cartilage surface (Grade 0) in this point is defined by an average roughness Ra lower than Rm µm, where the specific value of Rm may be validated by an expert consensus (for instance, Rm could be fixed at 20 µm). Similarly, an unobvious cartilage visual lesion with roughness greater than Rm will be labeled Grade 1. Naturally, this definition of normal cartilage surface may be improved and validated by expert consensus.

Introduction of an objective quantification inside the I.R.C.S. Hyaline Cartilage Lesion Classification System, by taking into account a parameter like roughness may improve, in an objective way, the identification of the beginning of cartilage disease, for which a therapy could be performed (hygieno dietetic treatment, for instance). In case of arthroscopic Autologous Chondrocyte Implantation, the roughness parameter could help the surgeon in the choice of his graft.

Similarly, cartilage thickness and defect depth or size may also be used to provide an objective score, or to quantify an existing score like the I.R.C.S. Hyaline Cartilage Lesion Classification System for grade 2, grade 3 and grade 4. For instance, the "normal" thickness around a defect may be defined as the mean thickness Tin for points at the vicinity at the defect border ideally graded 0 (thanks to roughness). Grade 2 may be then defined as a depth of the cartilage defect lower than Tm/2.0, Grade 3 as a depth greater than Tm/2.0 without bone breaking and grade 4, if a bone breaking exists. Alternatively, 'normal' thickness can also be estimated using the statistical model, which was built using anatomic data from normal specimens or patients.

The surface cartilage may thus be graded with such a quantified approach. For each obvious visual defect, the border of the defect can be defined with the pointer or imaging probe. Surface cracks or subsurface flaws can be identified, for example, with the Endoarticular interferometric non destructive imaging system. All of the surface cartilage inside the defect is then graded in a quantitative way with the same grading scheme (Grade 1 to 4). For no obvious visual defect, the cartilage is graded (Grade 0, Grade 1) with the roughness. Thus, for each point of the cartilage surface is available a grading from 0 to 4 based on objective quantification.

A global cartilage score may be computed by identifying, for instance, the relative percentage of each grade over the whole surface. Other cartilage parameters relating to internal structure, number or size of flaws, material strength or modulus, biochemical properties, fluorescence, etc. . . . may also be incorporated into the score. Such scores may be made in a semi-automated or automated way.

Figure 10:
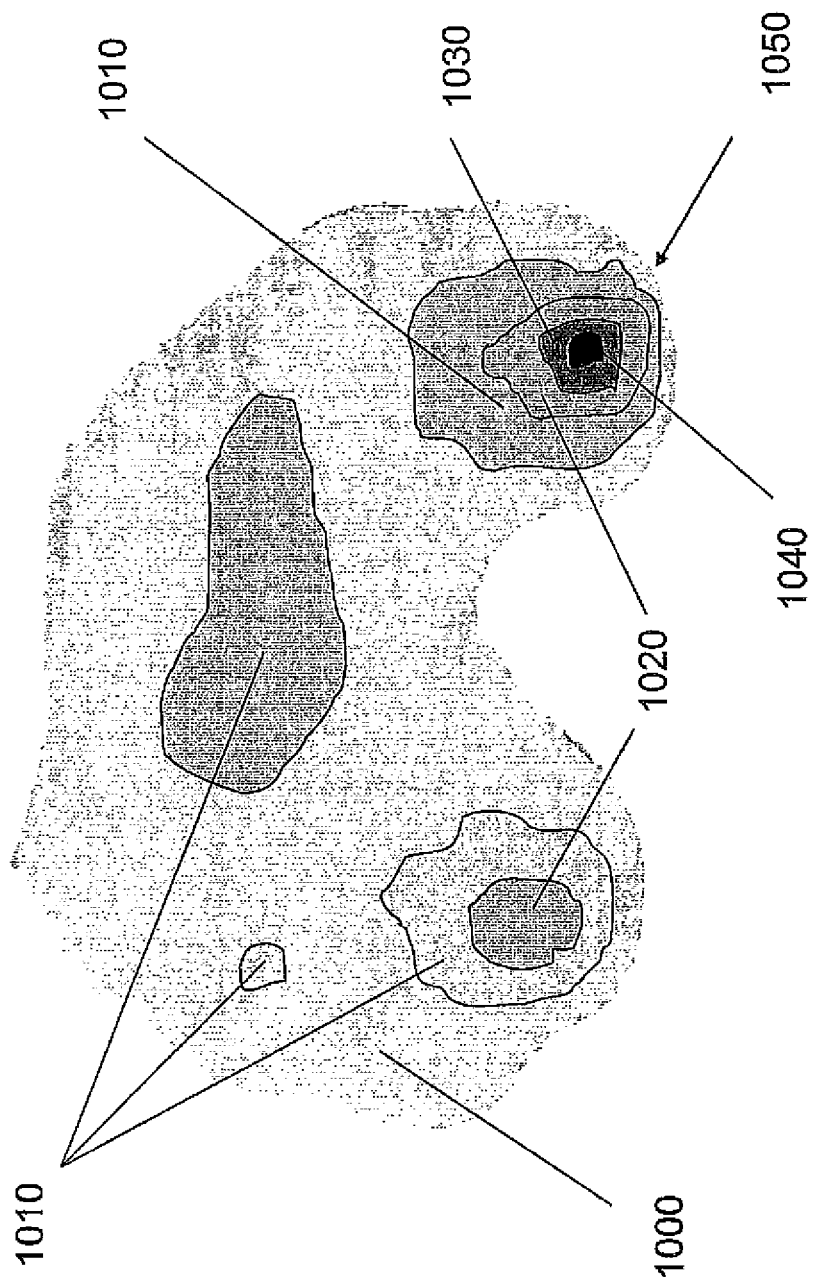
FIG. 10 is a cartilage quality parameter map.

Referring now to FIG. 10 one can see how cartilage parameters can be incorporated onto the osteo-cartilaginous model. These parameters can be individual parameters, such as a roughness, or combination of parameters, such as the grades of a score (e.g., 1000, 1010, 1020, 1030 and 1040, correspond to ICRS grade values 0, 1, 2, 3, and 4 respectively). These data can be used to help plan the cartilage intervention. An optimal implant type or shape can be determined by assessing the quality of the adjacent cartilage using the parameter map. Referring now to the medial condyle area 1050, the defect areas of 1040, 1030, and 1020 are visually identifiable and surrounded by a region 1010 which contains no visually observable defects, but was detected as having surface micro-flaws or fibrillations by one of the previously described tools. Using this quantitative information, the surgeon may decide to select or fashion a larger implant that restores the entire area defined by 1010 (and not only the visually obvious areas of 1020 to 1040). Alternatively, the surgeon can chose a different allograft site which better corresponds to the shape of the defect as defined by region 1010.

Speed of Ultrasound Calibration

Accurate quantification with ultrasound necessitates determining accurately the speed of ultrasound waves in the medium or tissue they are traveling through. This determination is implicitly included in the calibration step of the US probe for the material used to calibrate the probe. However, the speed of ultrasound is a function of environmental parameters (temperature, tissue density, tissue elasticity, etc.) which may affect its value. Automated calibration during the arthroscopic procedure would therefore be useful (for instance, to accurately evaluation of surface roughness). In a co-registered environment in which two imaging modalities are fused (MRI and US, for instance), the MRI can be used as a benchmark to calibrate the speed of sound in the various tissues of the US images. By using a 2D US image, the size of the image (pixel×pixel), transferred onto and scaled with the MRI, will enable the determination of the corresponding size in mm×mm of the ultrasound imaging pixel.

Roughness Improvement

Figure 8:
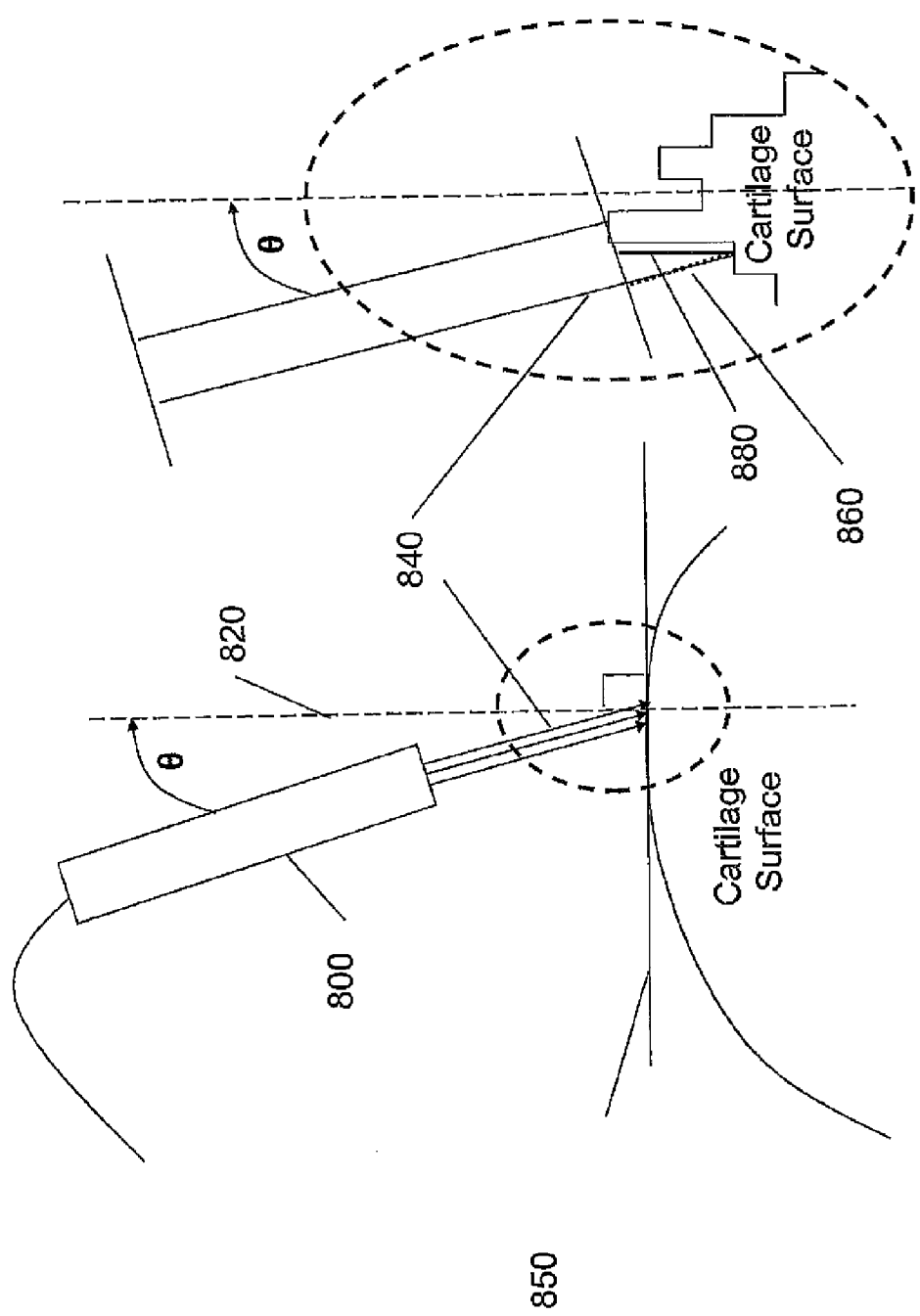
FIG. 8 illustrates a means for measuring roughness which is one qualitative measure of the quality of the cartilage.

The ultrasound roughness parameter has been previously introduced to characterize the quality of the cartilage tissue. Furthermore, this parameter is involved in the evaluation of the cartilage quality (cf. quality score) from which therapeutic decision are made. It is preferably defined with a high accuracy. Calculated by the method of the average roughness, the position of the incident beam relative to the surface must be taken into account to determine this parameter with accuracy. Indeed, in the real world, the ultrasound beam is not orthogonal to the tangent plane of the cartilage surface as it depends on how the surgeon or the robot holds the probe. FIG. 8 illustrates the inclination of the scan lines 840 relatively to the tangent plane 850 at the cartilage surface, in the plane of the ultrasound beam. In this plane, let $\theta$ be the angle between the scan lines 840 and the normal 820 at the tangent plane. The relative height between two adjacent scan lines is illustrated by the distance 860. As observed in the picture, this distance 860 is under-evaluated in comparison with the real one 880. A correction factor (such as $1/\cos\theta$) must be introduced to determine with accuracy the relative height between each scan line. Such an approach is not feasible without a navigated virtual environment.

In the same way, the ultrasound roughness parameter may also be determined from the angular distribution of the mean backscatter power. However, the method presented by Chiang et al. suffers from the necessity of scanning the same point of the cartilage surface from different position and angle to effectively compute this angular distribution. These geometrical constraints are not feasible in the real world, especially under arthroscopic conditions. We propose a new approach in a navigated environment. Using an intra-articular ultrasound probe P with a linear array of n piezoelectric elements (PE). And suppose the osteo-cartilaginous model initialized (205), the probe calibrated. At each time, the position of the n PE relatively to the cartilage surface is known. An angular record of the mean backscatter power for a point M0 may be done by: 1—determining the piezoelectric element PE0 which is the nearest from the cartilage surface; M0 is defined by the intersection of the scan line from PE0 with the cartilage surface—activating PE0 in alternative emitting and receipting mode; 3—activating simultaneously the other elements in reception mode to record the mean power backscattered by the unique scanned point M0 (and thus under different angles).

These two different approaches may be complementary. For instance, when the cartilage surface is too convex, it may be helpful to use the second approach which is not disturbed by the convexity of the cartilage surface. The first approach is a "local" approach, the second one is punctual.

Navigation and Robotics

In one embodiment, the system provides at least one other model for a second bone in the operated joint (for example, the tibia bone 4). This may be another deformable single or multi-layer osteo-cartilaginous model if the surgeon intends to assess and treat the cartilage on that bone. It could however be a simpler one (for example, defined by a few landmark points only) depending on the surgery. The model can be used to analyze the relative kinematics of the joint, to assess the position of the load line across the knee, to assess the joint stability (lachman, anterior drawer, varus/valgus stability testing, etc), and/or to calculate the relative contact areas and patterns between the articulating cartilage surfaces. This data may help to plan 235, modify and/or control the treatment. For example, it may be desired to correct, alter or monitored the leg alignment the same time as the cartilage procedure. Based on the displayed data the surgeon may chose to perform a high tibial or femoral osteotomy. The surgeon might select a more curved or pronounced graft to replace the condyle with, in order to modify the laxity in that compartment or to modify the relative position of the bones (for alignment or stability). The surgeon can also use the shape and curvature of the models to plan and control the placement of an implant or graft, such that the implant is sitting flush against the surrounding bone surface. An imaging device such as the ultrasound probe or arthroscope can be used to measure the flushness or gap between the implant and surrounding bone surface in order to optimize and control the placement without having to contact the surface directly.

The osteo-cartilaginous models may also be used to improve the quality of the cartilage data acquisitions. For example, the navigation system can help guide the surgeon to position the probe such that it is directly perpendicular to the cartilage surface (for example, the angle between the imaging plane and bone surface can be displayed). It is commonly known that the more perpendicular the beam is to the surface being imaged, the higher the receiving signal strength will be (incidence angle). The angular incidence may be taken into account during the roughness calculation, by considering the angle of the ultrasound beam relative to the surface. If the movement of the probe is automated, as for example with a 3D US probe, the control system could automatically orient the probe head such that it perpendicular to the surface at any point, while the surgeon is scanning over the bone surface. If a complete 3D image volume is acquired with the probe, the algorithm for extracting the cartilage parameter may use the osteo-cartilaginous model information to optimize the calculation (for example, using only the portion of the data-set that was acquired when the image plane was largely perpendicular to the bone surface to calculate the roughness parameter). Alternatively, this could be inferred by the image data itself (e.g., intensity or gradient information), or by combining the information from both sources.

Surgical instruments such as awls, scalpels, drills, saws, burr, etc. . . . may also be tracked, calibrated and navigated. Geometric surface models of the tool shape can be provided and visualized on the screen, relative to the bone and relative to a specific defined plan 235. In a multimodal environment, the therapist will have the possibility to switch between the different acquired modalities to improve the evaluation of the cartilage disease. The intersection of the tool and osteo-cartilaginous models can be calculated during the treatment, and the osteo-cartilaginous model can be updated 222 in real-time to reflect the alteration incurred by the tool (for example, the depth of penetration of a burr into the bone surface). Volumetric rendering (pixel based) methods may be used to speed up the real-time calculations (U.S. patent application Ser. No. 11/688,628 entitled Computer-Aided Osteoplasty Surgery System by Buly et al contains additional details on such methods and is hereby incorporated by reference in its entirety).

A robot may also be used to guide the surgical and cartilage data acquisition tools. This robot may be a conventional or haptic type robot that allows the surgeon to move the tool freely in predefined boundaries, but is prevented from entering areas outside the boundary (see, for example, US Patent Application No. 20060142657). The robot can be programmed to allow milling in an area defined by the shape and position of the planned implant or allograft harvest site, or by a boundary defined on the cartilage quality map (e.g., 1030 in FIG. 10).

Finally, all of the information collected and displayed during the procedure may be saved on a patient report (hospital network, CD-Rom, etc). This provides a record of what has been preformed and allows comparison with follow-up procedures, etc. . . . .

The following is an example that sets forth exemplary steps that can be carried out in accordance with a surgical procedure of one embodiment of the present invention: (1) calibrate tools; (2) attach bone trackers; (3) initialize osteo-cartilaginous model; (4) acquire cartilage data relative to initialized model; (5) morph model to cartilage position data and incorporate cartilage parameters into model; (6) calculate and display score; (7) navigate with respect to model; (8) plan treatment (e.g., position and size of implant or Autologous graft); (9) navigate treatment tools; (10) update model and score; (11) create report.

All abovementioned references are hereby incorporated in their entirety.

What is claimed is:

1. A computer-assisted orthopedic surgery system for performing joint preservation and assisting cartilage diagnostic and therapeutic procedures comprising:
    a cartilage data acquisition tool for acquiring cartilage data;
    a computer system configured to implement a three-dimensional osteo-cartilaginous computer model, the computer system having:
        a memory storing a computer program that, when executed, causes the computer system to
            extract at least two parameters from the acquired cartilage data that is indicative of a quality of the cartilage,
            incorporate the at least two parameters into the three-dimensional osteo-cartilaginous computer model,
            compute a synthetic cartilage quality score, wherein the synthetic cartilage quality score is a function of the at least two parameters, and
    a surgical treatment tool operably coupled to the computer system, the surgical treatment tool being configured for performing the joint preservation and assisting cartilage diagnostic and therapeutic procedures, the surgical treatment tool further configured to be navigated based on the three-dimensional osteo-cartilaginous computer model, wherein the computer system is configured to continuously update the three-dimensional osteo-cartilaginous computer model in real-time during the joint preservation and assisting cartilage diagnostic and therapeutic procedures based on the computed synthetic cartilage quality score, and further configured to display the synthetic cartilage quality score.

2. The computer-assisted orthopedic surgery system of claim 1, wherein the three-dimensional osteo-cartilaginous computer model comprises a model that includes cartilage data and bone data, including the morphology of cartilage, cartilage layers, bone and subchondral bone surfaces.

3. The computer-assisted orthopedic surgery system of claim 1, wherein one of the at least two parameters is a shape of a border of a cartilage defect, a depth of the defect, a volume of the defect, a theoretical thickness which is measured as a height of the remaining healthy cartilage surface, a texture or surface characterization of the cartilage, roughness of the cartilage, or pathological vascularization, a biomechanical property, an area ratio, or a detection of flaws in the cartilage.

4. The computer-assisted orthopedic surgery system of claim 1, wherein the computer program comprises software that when executed quantifies at least one of the following parameters selected from the group consisting of cartilage surface texture or roughness, a distance between the cartilage surface and the underlying subchondral bone, biomaterial properties of the cartilage, and cartilage subsurface ultra-structural and biochemical properties.

5. The computer-assisted orthopedic surgery system of claim 1, wherein the three-dimensional osteo-cartilaginous computer model is obtained using an imaging device and is stored and registered to a patient using data acquired at a time of examination or surgery.

6. The computer-assisted orthopedic surgery system of claim 1, wherein the three-dimensional osteo-cartilaginous computer model is an image-free deformable model that is registered to a patient using deformation techniques including bone morphing techniques resulting in the three-dimensional osteo-cartilaginous model being created at a time of surgery.

7. The computer-assisted orthopedic surgery system of claim 1, wherein the three-dimensional osteo-cartilaginous computer model is a 3D deformable double-layer model of a bone having an outer cartilage surface and an inner cartilage surface and an external bone surface and the acquired cartilage data includes images of the cartilage, wherein the images of the cartilage are segmented such that the outer cartilage surface and the inner cartilage surface are identified, with positions of these segments being known in a bone coordinate system.

8. The computer-assisted orthopedic surgery system of claim 1, wherein the computer system is further configured to visually display the extracted parameters on the three-dimensional osteo-cartilaginous computer model in real-time as the parameters are extracted.

9. The computer-assisted orthopedic surgery system of claim 8, wherein the computer system is further configured to display the extracted parameters utilizing a technique selected from the group consisting of: using color maps, using transparency, and using image fusion techniques where at least two different types of images or data sets are overlapped in a multimodal environment.

10. The computer-assisted orthopedic surgery system of claim 8, further configured to highlight on the three-dimensional osteo-cartilaginous computer model regions where data has been acquired to assist and guide a surgeon in acquiring cartilage data.

11. The computer-assisted orthopedic surgery system of claim 1, wherein the synthetic cartilage quality score is based on two or more acquired parameters: a thickness of the cartilage, a depth or size of an observed cartilage defect, and a computed surface cartilage grade.

12. The computer-assisted orthopedic surgery system of claim 1, wherein the three-dimensional osteo-cartilaginous computer model is continuously updated in real-time as cartilage data is acquired with the cartilage data acquisition tool, as the parameters are extracted, as the parameters are incorporated into the three-dimensional osteo-cartilaginous computer model, and as the surgical treatment tool is navigated.

13. The computer-assisted orthopedic surgery system of claim 1, wherein the cartilage data acquisition tool comprises a three-dimensional tracked ultrasound probe and one of the at least two parameters comprises a surface roughness of the cartilage.

14. The computer-assisted orthopedic surgery system of claim 1, wherein the cartilage data acquisition tool comprises a three-dimensional tracked ultrasound probe and one of the at least two parameters comprises a thickness of the cartilage.

15. The computer-assisted orthopedic surgery system of claim 1, wherein the cartilage data acquisition tool comprises a three-dimensional tracked calibrated endoarticular optical coherence tomography probe and one of the at least two parameters comprises a surface roughness of the cartilage.

16. The computer-assisted orthopedic surgery system of claim 1, wherein the cartilage data acquisition tool comprises a three-dimensional tracked endoarticular infrared probe and one of the at least two parameters is acquired by emitting infrared light, receiving reflected infrared light, computing an averaged spectroscopic signal, analyzing peaks of the signal and expressing health of the cartilage based on a ratio of a (detected signal peak) ($cm^{-1}$) to 1338 $cm^{-1}$.

17. The computer-assisted orthopedic surgery system of claim 1, wherein the cartilage data acquisition tool comprises a three dimensional tracked endoarticular fluorescent imaging system and the at least two parameters are acquired by introducing marked molecules into a target cartilage area of a patient and detecting the marked molecules with an arthroscopic unit that includes at least one intra-articular illumination device capable of emitting light at an adapted frequency and at least one intra-articular detector capable of detecting reflected fluorescence light.

18. The computer-assisted orthopedic surgery system of claim 1, wherein the computer system is further configured to map the at least two parameters onto the three-dimensional osteo-cartilaginous model in real-time as a surgery proceeds to assist a surgeon in deciding a course of action.

19. The computer-assisted orthopedic surgery system of claim 1, wherein the cartilage data acquisition tool is selected from the group consisting of: a tracked pointer, a tracked arthroscope, a tracked calibrated endoarticular optical coherence tomography probe, a tracked endoarticular infrared probe, a tracked endoarticular interferometric non-destructive laser imaging system, and a tracked endoarticular fluorescent imaging system.

20. A system for a computer-assisted orthopedic surgery for performing joint preservation and assisting cartilage diagnostic and therapeutic procedures, the system comprising:
- a cartilage data acquisition tool for acquiring cartilage data;
- a computer system configured to implement a computer generated three-dimensional osteo-cartilaginous computer model having a cartilage quality data map, the computer system having:
  - a memory storing a computer program that, when executed, causes the computer system to
    - extract at least one morphological parameter from the acquired cartilage data, the at least one parameter being indicative of a quality of the cartilage,
    - incorporate the at least one parameter into the three-dimensional osteo-cartilaginous computer model
    - compute a synthetic cartilage quality score based on the at least one morphological parameter and a secondary parameter indicative of the quality of the cartilage, and
- at least one surgical treatment instrument that is operably coupled to the computer system, the at least one surgical treatment tool being configured for performing the joint preservation and assisting cartilage diagnostic and therapeutic procedures, the at least one surgical treatment tool further configured to be navigated based on the three-dimensional osteo-cartilaginous computer model,
- wherein the computer system is configured to continuously update the cartilage quality data map of the three-dimensional osteo-cartilaginous computer model in real-time during the joint preservation and assisting cartilage diagnostic and therapeutic procedures based on the computed synthetic cartilage quality score, and further configured to display the synthetic cartilage quality score.

21. The system of claim 20, wherein the three-dimensional osteocartilaginous computer model comprises a model that includes cartilage data and bone data, including the morphology of cartilage, cartilage layers, and bone and subchondral bone surfaces.

22. The system of claim 20, wherein the at least one morphological parameter is selected from the group consisting of: a shape of a border of a cartilage defect, a depth of the cartilage defect, a volume of the cartilage defect, a theoretical thickness which is measured as a height of a remaining healthy cartilage surface, a texture or surface characterization of the cartilage, roughness of the cartilage, and pathological vascularization, a biomechanical property, an area ratio, or a detection of flaws in the cartilage.

23. The system of claim 20, wherein the computer program comprises software that when executed quantifies at least one of the following morphological parameters selected from the group consisting of cartilage surface texture or roughness, a distance between a cartilage surface and underlying subchondral bone, bio-material properties of the cartilage, and cartilage subsurface ultra-structural and biochemical properties.

24. The system of claim 20, wherein the secondary parameter is extracted from a preoperative image.

25. The system of claim 24, wherein the preoperative image is an MRI.

26. The system of claim 20, wherein the secondary parameter is extracted from intraoperatively acquired cartilage data.

27. A computer-assisted orthopedic surgery system for performing joint preservation and assisting cartilage diagnostic and therapeutic procedures, the system comprising:
- a position measuring system;
- a tool tracked by the position measuring system and configured to acquire cartilage and bone data;
- a computer configured to display a three-dimensional osteo-cartilaginous model having a cartilage quality data map, the computer having a memory storing a computer program that, when executed, causes the computer to
  - extract at least two parameters from the acquired cartilage data that is indicative of a quality of the cartilage,
  - incorporate the at least two parameters from the acquired cartilage data and bone data into the three-dimensional osteo-cartilaginous model,
  - compute a synthetic cartilage quality score that is a function of the at least two parameters, and
- a surgical treatment tool tracked by the position measuring system and operably coupled to the computer, the surgical treatment tool being configured for performing the joint preservation and assisting cartilage diagnostic and therapeutic procedures, the surgical treatment tool further configured to be navigated based on the three-dimensional osteo-cartilaginous computer model,
- wherein the computer system is configured to continuously deform the three-dimensional osteo-cartilaginous computer model in real-time during the joint preservation and assisting cartilage diagnostic and therapeutic procedures based on the acquired cartilage and bone data and the computed synthetic cartilage quality score, and further configured to display the synthetic cartilage quality score.

* * * * *